US012685718B2

(12) United States Patent
Pastor Porras et al.

(10) Patent No.: US 12,685,718 B2
(45) Date of Patent: Jul. 21, 2026

(54) FEED ADDITIVE

(71) Applicant: LUCTA, S.A., Madrid (ES)

(72) Inventors: Jose Javier Pastor Porras, Madrid (ES); Maria Gema Tedo Perez, Madrid (ES); Marta Blanch Saborit, Madrid (ES); Jose Sola Parera, Madrid (ES)

(73) Assignee: LUCTA, S.A., Madrid (ES)

( * ) Notice: Subject to any disclaimer, the term of this patent is extended or adjusted under 35 U.S.C. 154(b) by 802 days.

(21) Appl. No.: 17/915,007

(22) PCT Filed: Mar. 30, 2021

(86) PCT No.: PCT/EP2021/058261
§ 371 (c)(1),
(2) Date: Sep. 27, 2022

(87) PCT Pub. No.: WO2021/198235
PCT Pub. Date: Oct. 7, 2021

(65) Prior Publication Data
US 2023/0181503 A1     Jun. 15, 2023

(30) Foreign Application Priority Data

Mar. 31, 2020    (EP) ................................... 20382257

(51) Int. Cl.
| | |
|---|---|
| *A61K 31/192* | (2006.01) |
| *A23K 20/105* | (2016.01) |
| *A23K 20/111* | (2016.01) |
| *A23K 20/158* | (2016.01) |
| *A23K 50/30* | (2016.01) |
| *A23K 50/60* | (2016.01) |
| *A23K 50/75* | (2016.01) |
| *A61K 31/05* | (2006.01) |
| *A61P 1/00* | (2006.01) |

(52) U.S. Cl.
CPC .......... *A61K 31/192* (2013.01); *A23K 20/105* (2016.05); *A23K 20/111* (2016.05); *A23K 20/158* (2016.05); *A23K 50/30* (2016.05); *A23K 50/60* (2016.05); *A23K 50/75* (2016.05); *A61K 31/05* (2013.01); *A61P 1/00* (2018.01)

(58) Field of Classification Search
CPC .... A61K 31/192; A61K 31/05; A23K 20/158; A23K 50/30; A23K 50/60; A23K 50/75; A23K 20/105
USPC ....................................................... 514/572
See application file for complete search history.

(56) References Cited

U.S. PATENT DOCUMENTS

| | | | |
|---|---|---|---|
| 2007/0122505 A1 | 5/2007 | Elgaard et al. | |
| 2009/0324801 A1* | 12/2009 | Lopez De Hierro .. | A23K 50/30 426/655 |
| 2010/0113612 A1* | 5/2010 | Raederstorff ......... | A61K 31/05 514/734 |
| 2010/0116312 A1 | 5/2010 | Peumans et al. | |
| 2010/0204121 A1 | 8/2010 | Romero et al. | |

FOREIGN PATENT DOCUMENTS

| | | |
|---|---|---|
| CN | 102578387 A | 7/2012 |
| EP | 1994835 A1 | 11/2008 |
| EP | 2813221 A1 | 12/2014 |
| WO | 2007096446 A1 | 8/2008 |

OTHER PUBLICATIONS

Behnke Animal Feed Science Technology, 1996, 62, 49-57 (Year: 1996).*
Xie et al Food chemistry, 2019, 276, 662-674 (Year: 2019).*
International Search Report issued in corresponding International PCT Application No. PCT/EP2021/058261; Mailing Date: Jun. 30, 2021.
Pohl, et al.,; (2017). Early weaning stress induces chronic functional diarrhea, intestinal barrier defects, and increased mast cell activity in a porcine model of early life adversity. Neurogastroenterology % Motility. E13118. DOI. 10.1111/nmo.13118.
Rufino-Palomares, E, et. al., Maslinic acid, a natural triterpene, and ration size increased growth and protein turnover of white muscle in gilthead sea bream (*Sparus aurata*). Aquac. Nutr. 18, 568-580 (2012).
Peng Mengfei et al, "Polyphenols and tri-terpenoids from Olea europaea L. in alleviation of enteric pathogen Infections through limiting bacterial virulence and attenuating inflammation", Journal of Functional Foods, Elsevier BV, NL, (Jul. 6, 2017), vol. 36, pp. 132-143, doi: 10.1016/J.JFF.2017.06.059, ISSN 1756-4646,.
EFSA Journal, Scientific Opinion concerning a Multifactorial approach on the use of animal and non-animal-based measures to assess the welfare of pigs; 2014;12(5):3702.
Welface Quality Assessment protocol for pigs; http://www.welfarequalitynetwork.net/en-us/reports/assessment-protocols/.

* cited by examiner

*Primary Examiner* — Yevgeny Valenrod
(74) *Attorney, Agent, or Firm* — Chrisman Gallo Tochtrop LLC

(57) ABSTRACT

Present invention relates to the use of hydroxytyrosol (HT), maslinic acid (MA) and oleanolic acid (OA) as additive in feed for a domesticated animal at very early days of life or from birth. The invention provides an additive with particular amounts of these three ingredients and an additivated feedstuff ready to use comprising said additive.

9 Claims, 4 Drawing Sheets

(A)

(B)

(A)

(B)

FEED ADDITIVE

CROSS-REFERENCE TO RELATED APPLICATIONS

This is a National Stage application of PCT international application PCT/EP2021/058261, filed on Mar. 30, 2021, which claims the benefit of European Patent Application EP20382257.2 filed on Mar. 31, 2020, both of which are incorporated herein by reference in their entirety.

TECHNICAL FIELD

Present invention relates to the field of feed additives for animal nutrition to improve the performance and welfare of the livestock and to obtain high quality animal-source foods.

BACKGROUND ART

One of the main problems focused by animal breeders, in particular by farm animal breeders (i.e., cattle, pig, broilers, turkeys, sheep, etc.) is the mortality at first stages of the animal life. Mortality in early life is usually due to nutritional, environmental and/or immunological challenges commonly present in the production cycle that negatively affect animal productivity and welfare. Common stressors present in the life cycle include weaning in mammals (e.g., pigs), human interventions (e.g., vaccination procedures in mammals and birds), mixing animals from different origin and groups (e.g., cross fostering in mammals) and dietary changes. For these reasons, breeders usually require the use of certain antimicrobials and/or other feed additives and/or feed ingredients, such as vitamins, in feed and/or in drinking water in order to ensure an early life survival and further growth to guarantee the biggest number of animals in good health reaching the final weight to market.

In the particular case of swine, piglets usually show intestinal disturbances after weaning, when the intestine is still immature, as part of the inflammatory response triggered by several stressors. If the response is severe, it can eventually cause the death of the animal (and loses for the breeder). A similar pathological scenario is viewed in broilers. Thus, animals tend to regularly receive veterinary treatments during the first stages of life, as previously indicated. Administration of substances with antimicrobial effect through the feeding is a common practice, but animals usually detect the presence of these and other substances and reduce the intake of feed. This reduction of intake due to palatability problems is added to the inherent stress conditions associated with weaning in mammals, that have to get use to a solid or semi-solid feed different from mother's milk, but also associated with other stress conditions previously enumerated (vaccination, mixing and diseases). The final result is that the daily weight gain and/or the feed conversion ratio are reduced, and achievement of market weight is lowered with the accompanying costs for breeders.

In spite of the utility of certain antimicrobials and other supplements, trends in the breeding field aim to reduce their administration for evident reasons. Main are related with the evidences about the relationship between their use and the increased number of antibiotic-resistance bacteria strains registered in the last decades, with adverse immune system reactions (hypersensitivity or allergy) and other secondary effects of certain molecules administered to immature living beings. Other reasons are also related with the refusal of the final consumers to acquire animal products coming from animals fed with medicated diets.

A number of feed additives have been developed to assist in boosting the animals' immune system, regulate gut microbiota, and reduce negative impacts of weaning in mammals and other challenges. The most commonly used feed additives include acidifiers, derivatives of zinc and copper, prebiotics, probiotics, yeast products, nucleotides, and plant extracts.

One example of composition being administered to animals (broilers and pigs) for promoting digestion and absorption of nutrients is disclosed in the Chinese patent application CN102578387 (BEIJING DABEINONG TECH GROUP). In this document an acidifying agent including several acids is proved to be effective to shorten slaughter time, protect the health of the gastrointestinal mucosa of animals, enhance the immune function of animals, and prevent diseases. As indicated, addition of certain acids in animal feed causes rejection of the same. Although data in CN102578387 seem to demonstrate good daily weight gains, and it is indicated that palatability of feed is not altered, tested animals were not in a context of disease and/or stress, in which feed intake is moreover reduced for this reason, leading to low final body weight in case of survival, or to death if no treatment is applied. Even in case of treatment, the final body weight can be low in relation with animals that did not suffer any disease.

Thus, in spite of existing efforts, there is still a need in the field of alternatives allowing to reduce the dependency in use of antimicrobials and other supplements aiming good performance of animal growth, in particular in early stages of their lives.

SUMMARY OF INVENTION

Testing with different olive extracts and pure compounds included in these extracts, inventors surprisingly found a combination of three active ingredients that, once added in animal feed at low concentrations, allowed good performance of animals in terms of reducing mortality in poultry, from birth to slaughterhouse, and in mammals (pigs), from lactation to after weaning, from creep-feed or prestarter to starter feeds. Good daily weight gain in mammals and poultry was also observed, as well as good total final weight gain, even in case of a very low initial weight, and good protection against intestinal dysfunction, microbial intestinal infections and diarrhoea. All this was in particular due to the unexpected adequate feed intake by the very young animals at stages of life with high vulnerability, in spite of the presence of ingredients known to reduce feed consumption for several reasons, in particular, due to aversive taste.

In addition, inventors could provide evidence that observed activity was related with stabilization of activated mastocytes, linked with a lower inflammatory response and with an improved intestinal barrier.

Thus, it is disclosed herewith the combined use of hydroxytyrosol (HT), maslinic acid (MA) and oleanolic acid (OA) as additive in feed for a domesticated animal.

This combined use of hydroxytyrosol (HT), maslinic acid (MA) and oleanolic acid (OA) is disclosed as an additive in feed for a piglet and/or a weaner. Data in examples show that when said combined used is administered to the piglets and/or weaners according to particular schedules of administration, the previous effects are highly promoted (i.e., good performance, good daily weight gain, protection against infections, etc.)

This combined use of hydroxytyrosol (HT), maslinic acid (MA) and oleanolic acid (OA) is also disclosed as an additive in feed for poultry. Again, when said combined used is administered to poultry according to a particular schedule of administration, the previous effects are highly promoted.

The three ingredients are, in combination, used as additives in the feed for young domesticated animals from birth and/or from weaning prior to the rearing or finisher phases. In terms of days of age, this means from 0 days of life (i.e., at birth) to around 70 days after birth in mammals, in particular in pigs, and from 0 days of life to 35 days after birth (i.e. hatch) in broilers, and from 0 days of life to 84-112 days after birth (i.e. hatch) in turkeys.

Effectively, as will be depicted in examples below, piglets and weaners and poultry receiving feed additivated with these three ingredients gave better results in terms of mortality indexes/percentages, medial (average) daily weight gain, final body weight before starting an adult fattening or finisher diet, and better control of inflammation and better nutrient absorption, in relation with controls not receiving the additivated feed in any of the above-mentioned diet phases. Tests were in addition performed in different stress conditions including challenging with pathogens and/or related immunogenic parts (i.e., lipopolysaccharides, LPS) and/or social stress and/or stress induced due to weaning and multiple changes of diet.

Moreover, these three active ingredients supposed a simplified mode to obtain good results in the field of animal growing, in relation with prior art alternatives including complex mixtures of additives or the administration of antimicrobials.

Furthermore, the combined use of these three ingredients was effective in animals of very low weight at birth and after weaning in the case of pigs and other mammals. The additive allowed an average body weight gain higher than expected in these kinds of very small animals.

Moreover, veterinary treatments required for the animals at these very sensitive stages of their lives could be reduced in a high extent.

Even another advantageous aspect of the combined used of these ingredients is that, in case of pigs (swine), they could be administered to the offspring of different genetic background of pigs (e.g., DanBred crossbred, (LargeWhite× Landrace)×Pietrain, Duroc crossbred, Hypor, PIC, and Topigs).

As previously described in literature, activation of mast cells is usually associated to inflammation and severe diarrhoea episodes and thus, prevention of mastocyte degranulation can eventually lead to a reduction in diarrhoea incidence (see Pohl et al. (2017). Early weaning stress induces chronic functional diarrhea, intestinal barrier defects, and increased mast cell activity in a porcine model of early life adversity. *Neurogastroenterology% Motility*. E13118. DOI. 10.1111/nmo.13118). Thus, invention also relates to the combination of hydroxytyrosol (HT), maslinic acid (MA) and oleanolic acid (OA) for use in the prevention of diarrhoea and/or pathogen infections of the gastrointestinal tract in a domesticated animal at a diet phase from birth and/or weaning prior to a rearing or finisher phase diet (comprising one or more different diets), derived from its mastocyte stabilizing activity. In other words, for a population of animals, defined according to their age, at a diet phase comprising, from day of birth to a day prior to the start of a rearing or finisher diet. This can also be disclosed as the use in combination of hydroxytyrosol (HT), maslinic acid (MA) and oleanolic acid (OA) for the preparation of a composition for the prevention of diarrhoea and/or pathogen infections of the gastrointestinal tract in a domesticated animal population as above defined. Invention also relates to a method for preventing diarrhoea and/or pathogen infections of the gastrointestinal tract in a domesticated animal population as above defined, comprising administering an effective amount of a composition comprising hydroxytyrosol (HT), maslinic acid (MA) and oleanolic acid (OA).

It is a first aspect of the invention an additive for domesticated animal feed, comprising hydroxytyrosol, maslinic acid, and oleanolic acid, in which the percentage by weight of hydroxytyrosol is from 0.3% to 5.0%, the percentage by weight of maslinic acid is from 2.0% to 20% w/w, and the percentage by weight of oleanolic acid is from 0.5% to 15% w/w, all percentages in relation with the total weight of the additive.

As will be illustrated in the examples, this additive can be liquid or solid.

Inventors propose, as particular embodiments of the first aspect, new solid additives for feeds comprising these three ingredients, which are additives for domesticated animal feed, said additives comprising hydroxytyrosol, maslinic acid, oleanolic acid and a binder to reduce dustiness, in which the percentage by weight of hydroxytyrosol is from 0.3% to 5.0%, the percentage by weight of maslinic acid is from 2.0% to 20% w/w, and the percentage by weight of oleanolic acid is from 0.5% to 15% w/w, all percentages in relation with the total weight of the additive, and wherein the additive is in particulate form with a mean particle size higher than 500 µm, and where more than 70% of the particles have a particle diameter higher than 400 µm and less than 30% of the particles have a particle diameter lower than 250 µm.

With these particular percentages of the three active ingredients in the additive, appropriate amounts can be added in any diet from birth prior to the rearing or finisher phase to get the final effective amounts in final feedstuff. Moreover, the combination of ingredients reduces losses during manufacturing, more in particular when the additive is solid and in the particulate form and at the same time a homogeneous additive is obtained, allowing so the accurate addition of the ingredients in a final feedstuff.

New feedstuffs have also been developed to cover the feeding of animals at these very sensitive stages of life, from birth until reaching the adult phase when adult diets are applied (i.e., rearing or finishing/fattening diets).

Therefore, the invention includes additivated feedstuffs (additivated domesticated animal feed) comprising the additive as defined above, and wherein the ratio of the weight of maslinic acid and of hydroxytyrosol (MA/HT) in the final feedstuff is from 2 to 20 and the ratio of the weight of maslinic acid and of oleanolic acid (MA/OA) in the final feedstuff is from 1 to 10.

This can also be defined as a feedstuff comprising the additive as defined in the first aspect, and wherein the ratio of the weight of maslinic acid and of hydroxytyrosol (MA/HT) in the final feedstuff is from 2 to 20 and the ratio of the weight of maslinic acid and of oleanolic acid (MA/OA) in the final feedstuff is from 1 to 10.

Or alternatively, the additivated feedstuff (animal feed) can be defined as comprising the additive as defined in the first aspect above, and comprising in the final feedstuff hydroxytyrosol at a concentration from 2.5 ppm to 20 ppm, maslinic acid at a concentration from 10 to 75 ppm, and oleanolic acid at a concentration from 5 to 35 ppm.

Thus, another aspect of the invention is an additivated feedstuff comprising the additive as defined above in the first aspect, wherein the ratio of the weight of maslinic acid and of hydroxytyrosol (MA/HT) in the final feedstuff is from 2 to 20 and the ratio of the weight of maslinic acid and of oleanolic acid (MA/OA) in the final feedstuff is from 1 to 10, and wherein:

(a) the feedstuff comprises an amount of additive giving HT at a concentration from 2.5 ppm to 20 ppm, MA at a concentration of at least 10 ppm and up to 75 ppm, and a concentration of OA of at least 5 ppm and up to 35 ppm, all concentrations in relation to the total weight of the feedstuff; or alternatively (b) the feedstuff comprises the additive, which comprises a binder, and said additive is in particulate form with a mean particle size higher than 500 µm, and where more than 70% of the particles have a particle diameter higher than 400 µm and less than 30% of the particles have a particle diameter lower than 250 µm; or alternatively (c) the feedstuff comprises an amount of additive giving HT at a concentration from 2.5 ppm to 20 ppm, MA at a concentration of at least 10 ppm and up to 75 ppm, and a concentration of OA of at least 5 ppm and up to 35 ppm, all concentrations in relation to the total weight of the feedstuff, and said additive is the one that comprises a binder and that it is in particulate form with a mean particle size higher than 500 µm, and where more than 70% of the particles have a particle diameter higher than 400 µm and less than 30% of the particles have a particle diameter lower than 250 µm.

When in this description the concentration or weight of any of HT, MA and OA in the feedstuff is mentioned, for example, is to be understood as the concentration or amount of hydroxytyrosol, maslinic acid and oleanolic determined by Liquid Chromatography coupled to Mass Spectrometry (LC-MS). In particular, determinations of the said concentrations/amounts are performed in a UPLC I-Class (Waters, Milford, USA) connected to a Xevo QT of MS detector (Waters, Milford, USA). Separation is performed using $H_2O$ (0.1% formic acid) and a 1:1 mixture of ACN:MeOH (0.1% formic acid) as solvents on a Kinetex 2.6 µm EVO C18 (2.1×100 mm, 100 A) column with a linear gradient. Detection is performed in negative mode and compounds are quantified by area comparison with the area of calibration curves made with real standards of known concentration or amounts.

Maslinic acid ((2α,3β)-2,3-Dihydroxyolean-12-en-28-oic acid) or crategolic acid is a compound derived from dry olive-pomace oil (an olive skin wax) which is a byproduct of olive oil extraction. It is a member of the group of triterpenes known as oleananes. It exerts a wide range of biological activities, such as antitumor, antidiabetic, antioxidant, cardioprotective, neuroprotective, antiparasitic and growth-stimulating. It is sold as a compound with high grades of purity (98%) or as an ingredient in extracts of olive fruit and olive leaves. When in present description "maslinic acid" is used it is to be understood as encompassing the acid form or any edible acceptable, salt or ester of the same.

Oleanolic acid or oleanic acid ((4aS,6aR,6aS,6bR,8aR, 10S,12aR,14bS)-10-hydroxy-2,2,6a,6b,9,9,12a-heptamethyl-1,3,4,5,6,6a,7,8,8a,10,11,12,13,14b-tetradecahydropicene-4a-carboxylic acid) is a naturally occurring pentacyclic triterpenoid related to betulinic acid. It is widely distributed in feed and plants where it exists as a free acid or as an aglycone of triterpenoid saponins. Oleanolic acid can be found in olive oil, *Phytolacca americana* (American pokeweed), and *Syzygium* spp, garlic, etc. It was first studied and isolated from several plants, including *Olea europaea* (leaves, fruit), *Rosa woodsii* (leaves), *Prosopis glandulosa* (leaves and twigs), *Phoradendron juniperinum* (whole plant), *Syzygium claviflorum* (leaves), *Hyptis capitata* (whole plant), *Mirabilis jalaps* and *Ternstroemia gymnanthera* (aerial part). Other *Syzygium* species including java apple (*Syzygium samarangense*) and rose apples contain it. Oleanolic acid is relatively non-toxic, hepatoprotective, and exhibits antitumor and antiviral properties. It is usually distributed as a compound with a high purity or as an ingredient in extracts of olive fruit and olive leaves, among other plant species. When in present description "oleanolic acid" is used it is to be understood as encompassing the acid form or any edible acceptable, salt or ester of the same.

Hydroxytyrosol (3,4-dihydroxyphenylethanol) is a phenylethanoid, a type of phenolic phytochemical with antioxidant properties in vitro. In nature, hydroxytyrosol is found in olive leaf and olive oil, in the form of its elenolic acid ester oleuropein and, especially after degradation, in its plain form. Hydroxytyrosol itself in pure form is a colourless, odourless liquid. The olives, leaves and olive pulp contain large amounts of hydroxytyrosol (compared to olive oil), most of which can be recovered to produce hydroxytyrosol extracts. It is proposed as a life prolonging agent according to assays performed in *Drosoplila melanogaster* (see US patent application US2010/0116312). It is also known as potent anti-oxidant. It is commercially available in several grades of purity or also as an ingredient in extracts of olive fruit and olive leaves. When in present description "hydroxytyrosol" is used it is to be understood as encompassing the alcohol or any edible acceptable, salt or ester of the same. Esters of hydroxytyrosol are acetates or gucuronide conjugates. An example of an ester of hydroxytyrosol is oleuropein.

Another aspect of the invention is the use of an additive as defined in the first aspect, or of an additivated feedstuff as defined in the second aspect, in a feed for a domesticated animal.

DETAILED DESCRIPTION OF THE INVENTION

Figure 1:
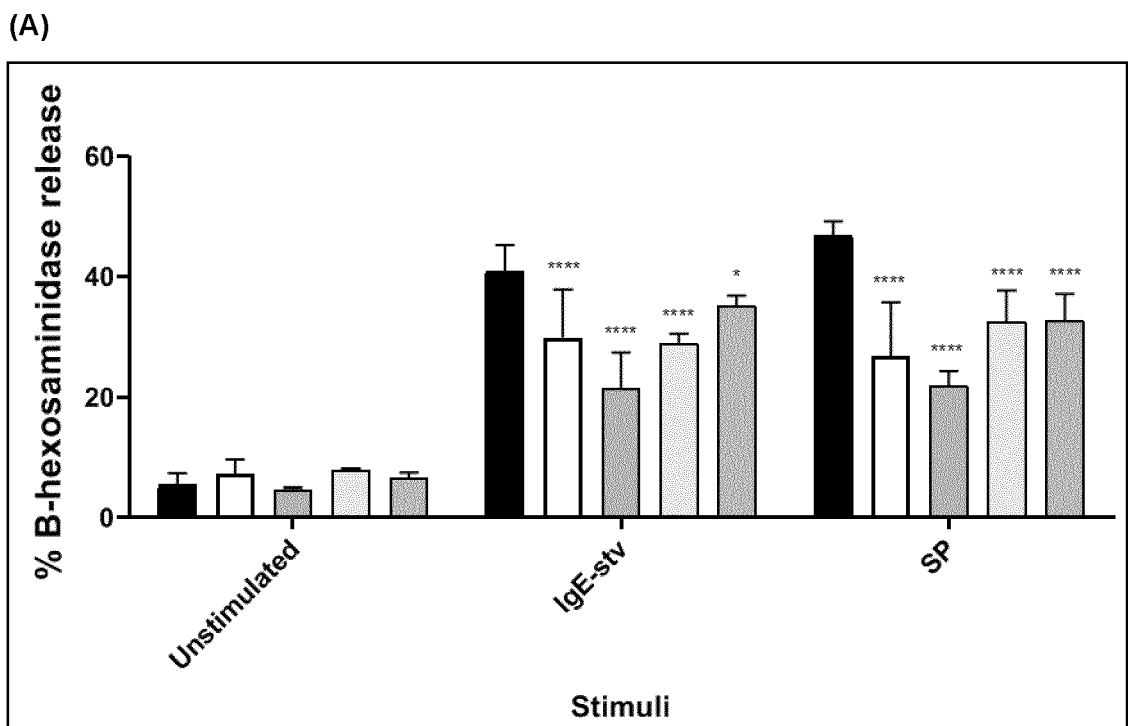
FIG. 1 shows % of B-hexosaminidase release (FIG. 1A) and the percentage of CD63 positive cells (FIG. 1B) for LAD2 cells submitted to different stimuli: unstimulated; challenged with doses of inmunoglobulin E (IgE-stv), related to allergic responses; and challenged with substance P (SP). Control (DMSO), left bar in each set, Cromolyn (100 µM) second bar in the set, a mixture of pure compounds at a weight ratio HT:MA:OA 14:50:12 (100 µg/mL) as the third bar in each set, formulation A with HT:MA:OA at ratio 9:50:23 (100 µg/mL) and formulation B with HT:MA:OA at ratio 8:50:23 (100 µg/mL), represented respectively by the fourth and fifth bars in each set.
Figure 1:
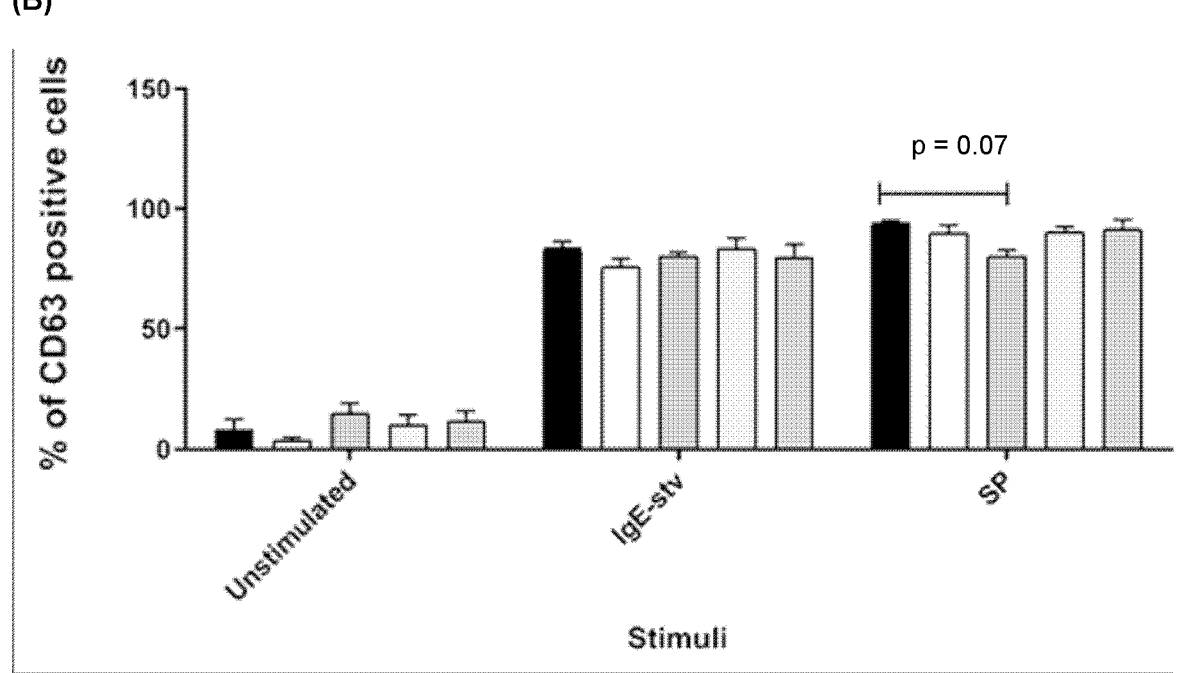

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As used herein, the indefinite articles "a" and "an" are synonymous with "at least one" or "one or more." Unless indicated otherwise, definite articles used herein, such as "the" also include the plural of the noun.

The term "domesticated animal" and "livestock animal" are used as synonymous in this description. Both relate to non-human animals raised in an agricultural setting or in farms to produce animal-derived commodities such as meat, eggs, milk, fur, leather, and wool. In present invention the following animals are considered under the domesticated animal or livestock animal category: ruminants, such as cattle, sheep and goats, pigs, horses, poultry, such as broilers, turkeys, geese or ducks, and fish.

In livestock production the so-called cycle of animal production (livestock) includes several phases that can be defined by the diet or feed the animal is consuming at certain days or weeks of life. Thus, these phases are also known as diet phases and reflect the animal age. Age of animal at different phase diet depends on the animal type, and these diet phases include from birth day (i.e. from hatching in non-mammal, such as poultry) and/or suckling/nursing (i.e. in mammals) up to the age in which an adult diet is started. Diet and feed are used as synonymous in this description.

Among the several livestock animals, different diet phases receive different names, making difficult harmonization.

The term "birth phase diet" according to this description encompasses the period or stage of livestock production from 0 days of life (i.e., at birth) to the time point in which a change of the diet is applied for any reason, weaning in mammals, or change to a so-called growing stage in broilers. In the particular case of mammals, birth phase diet includes nursing and optionally creep-feeding. "Creep-feeding" (also called creep-feed in piglets or starter feed in ruminants) is a method of supplementing the diet of young livestock by offering feed to animals that are still nursing or are milky fed. The composition of birth phase diets can vary with the price of the various components, but it is usually has a base of cracked corn, rolled oats, alfalfa, brewer's grain or any combination of these four. Other ingredients can include rolled barley, soybean meal, soybean hulls, molasses, dicalcium phosphate and mineral salts. In the case of piglets, diets based on thermal-treated cereal sources, protein concentrates from animal and/or vegetal origin, sources of lactose or any combination of these three is also common.

A "prestarter phase diet" usually corresponds to phase where the first dry diet is offered in the post-weaning stage in mammals. In the particular case of pigs, the prestarter diet is for weaned pigs at 3-4 weeks of age. They are very complex mixtures and they include dried milk products (lactose, dried whey and dried skim milk). Weaners are usually self-fed prestarter diets until they are 5 to 6 weeks of age. These diets can also be used as creep feed for young pigs still nursing the sow.

"Starter phase diet" includes the starter diet, usually for pigs weaned at 5-6 weeks of age, or as second feed in pigs weaned at 3-4 weeks of age, usually until the weaners are 18 Kg-20 Kg body weight. In broilers, a starter diet is for individuals usually from 0 to 10 days post-hatching. In turkeys, a starter diet is for individuals usually from 0 to 21/28 days post-hatching.

The later adult stage or adult phase is called in this description "rearing phase diet" (frequently used in a mammal context) or "finishing phase diet" (used mainly in poultry), although it may include as object either the fattening of the animals (i.e. for meat consumption), or the production of animal-derived commodities (i.e. eggs, milk, etc.). In pigs, the rearing phase comprises the grower (is up to approximately 55 kg of animal live weight) and fattening/finisher stages (up to market weight). Growers are fed a ration that is high in protein; whereas fibre content is increased in the porker ration. In broilers, a grower diet or different grower diets are administered since 11 until 22/35 days of life, and then different finishing diets can be employed, until approximately 35/42 days of life (sometimes more). In turkeys, a grower diet or different grower diets are administered since 21/28 until 84 days of life, and then different finishing diets can be employed, until approximately 112/140 (sometimes more). Within this "rearing or finishing phase diet" the skilled person in the art will understand farrow diet phases (for swine) and lactating diet phases in mammals are also included.

The expression "comprises at least one diet change" means that the composition of whatever being feed (diet) administered to livestock animals at that phase is changed, for example to reduce the protein content, or to increase vitamin supplementation.

As will be shown in the examples below, the combined use of hydroxytyrosol, maslinic acid and oleanolic acid as an additive in feedstuff is for animals that are catalogued as young non-reproductive animals, thus animals at a non-reproductive age. The term "young non-reproductive animal" means that the animals in question are not in an adult phase, but in a phase in which they are still sexually immature for reproduction.

Along this description, the following definitions have been applied to the different animal categories as set in EFSA Journal 2014; 12(5):3702 and/or http://www.welfare-qualitynetwork.net/en-us/reports/assessment-protocols/inl-cuding the categories and definition of target animals Finishing pig (*Sus scrofa domestica*): former growing pigs at the slaughterhouse, ready to be slaughtered (from 90 to 120 Kg, but locally up to 150 Kg)

Growing pig (*Sus scrofa domestica*): Pig raised with the purpose of meat production or reproduction, from 10 weeks old until it is ready for slaughter.

Rearing pig (*Sus scrofa domestica*): pig from 10 weeks to slaughter or service. Includes growing and finishing pigs.

Weaner (*Sus scrofa domestica*): a young pig from the time of weaning from its mother to 10 weeks at which time (plus or minus 2 weeks), pigs are commonly moved to a different accommodation. In the commonest breeds of pigs this weight range is 5-35 Kg BW.

Piglet (*Sus scrofa domestica*): Pig from birth until weaning.

The term "broiler" relates to chickens for fattening or reared for laying. In this description the three ingredients (HT, MA and OA) are given to broilers at a non-reproductive age, thus at an age or diet phase from hatch and up to 35 days post-hatch.

The term "turkey" relates to turkeys raised for fattening or reared for breeding. In this description the three ingredients (HT, MA and OA) are given to young turkeys non still for reproductive purposes, thus from hatch to 84 days post-hatch.

"Conversion index" is defined as the mass of consumed feed per mass of gained weight. Other indicators of the development of animals are the final body weight at a prescribed age, and the daily weight (or mean weight) gain indicated as g of gained weight per day. "Daily weight gain" or "average daily weight gain" (used as synonymous) is calculated as the difference of weight at two particular selected dates in relation with the test days between dates (i.e. [last weight-initial weight]/test days). "Average feed intake" is the mass of consumed feed per day.

The term "percentage of mortality" relates to the number of observed deaths in a group in relation with the total number of individuals in the group.

The term "percentage by weight" is also expressed as "w/w" and relates to the mass amount of a compound in relation to the total mass of the composition.

When in present description it is said "feed for the domesticated animal" is to be encompassed the final feed being ingested by animals, including feedstuffs, formulations or mixtures of ingredients containing the nutrients needed at each stage of life. The animal feed or feedstuffs include liquid preparations, as those usually administered while nursing in mammals (i.e., some creep-feed preparations), or solid powders or pelletized preparations.

The expression "effective amount" as used herein when relating to the amount of the ingredients hydroxytyrosol, maslinic acid, and oleanolic acid, refers to the amount of the compound that, when administered, is sufficient to promote daily weight gains of interest and intestine maturity and nutrient absorption and feed intake in young domesticated animals. The particular dose of compound administered according to this invention will of course be determined by the particular circumstances surrounding the case, including the compound administered, the route of administration, the particular condition being treated, and the similar considerations.

The expression "acceptable carriers" refers to edible (i.e. than can be ingested) acceptable materials, compositions or vehicles. Each component must be acceptable in the sense of being compatible with the other ingredients of the composition. It must also be suitable for use in contact with the tissue or organ of domesticated animals without excessive toxicity, irritation, allergic response, immunogenicity or other problems or complications commensurate with a reasonable benefit/risk ratio.

In several sections all along the description the amount of any of HT, MA or OA is expressed as "parts per million", ppm, (parts-per-million, $10^{-6}$), which relates to the mass fraction of the compound in the total weight of composition wherein it is contained (i.e. feedstuff). In chemistry, the mass fraction of a substance within a mixture is the ratio $w(i)$ of the mass $m(i)$ of that substance to the total mass $m(tot)$ of the mixture. So that when in present description MA is at 50 ppm, this means that in 1 ton of final composition (i.e. feedstuff) there are 50 g of MA (or 50 mg in 1 Kg).

The "ratio of the concentration" or "the ratio of the weight" between two or more compounds is the mass or weight ratio, thus the ratio between the weight (in mass units) of the compounds in the total weight of the composition.

The term "particle" as used herein, refers to a particle with at least two dimensions at the microscale, particularly with all three dimensions at the microscale (1 micrometers to 4000 micrometers). As regards the shape of the nanoparticles described herein, there are included spheres and polyhedral. In a particular embodiment the particle is spherical.

As used herein, the term "size" (i.e. particle size) refers to a characteristic physical dimension. For example, in the case of a particle that is substantially spherical, the size of the particle corresponds to the diameter of the particle. When referring to a set of particles as being of a particular size, it is contemplated that the set of particles can have a distribution of sizes around the specified size. Thus, as used herein, a size of a set of particles can refer to a mode of a distribution of sizes, such as a peak size of the distribution of sizes. In addition, when not perfectly spherical, the diameter is the equivalent diameter of the spherical body including the object. The particle size distribution is measured by laser difraction particle size analysis (Beckman Coulter). The term "mean particle size" according to this description is the mathematical expectation or average of all discrete particle sizes.

As previously indicated, is a first aspect of the invention, an additive for domesticated animal feed, comprising hydroxytyrosol, maslinic acid, and oleanolic acid, in which the percentage by weight of hydroxytyrosol is from 0.3% to 5.0%, the percentage by weight of maslinic acid is from 2.0% to 20% w/w, and the percentage by weight of oleanolic acid is from 0.5% to 15% w/w, all percentages in relation with the total weight of the additive.

Also as previously indicated, in a particular embodiment of the first aspect of the invention, the additive for domesticated animal feed is that comprising hydroxytyrosol, maslinic acid, oleanolic acid and a binder, in which the percentage by weight of hydroxytyrosol is from 0.3% to 5.0%, the percentage by weight of maslinic acid is from 2.0% to 20% w/w, and the percentage by weight of oleanolic acid is from 0.5% to 15% w/w, all percentages in relation with the total weight of the additive, and wherein the additive is in particulate form with a mean particle size higher than 500 μm, and where more than 70% of the particles have a particle diameter higher than 400 μm and less than 30% of the particles have a particle diameter lower than 250 μm.

This additive comprising the three ingredients in the indicated percentages or proportions is conceived as a composition helping nutrition of animals in sensitive stages of their lives (i.e., young animals), since it promotes intestine maturity.

The additives of the first aspect and the other corresponding embodiments listed below are applicable to provide the combined use of the three ingredients HT, MA and OA. Thus, they can be added in the effective amounts to the feed for domesticated animals.

In a particular embodiment of the feed additive, the percentage by weight of hydroxytyrosol is from 0.3% to 3.0% w/w, the percentages in relation with the total weight of the additive.

In another particular embodiment, optionally in combination with any embodiments above or below of the additive of the invention, the percentage by weight of maslinic acid is from 5.0% to 12% w/w, the percentages in relation with the total weight of the additive.

In also another particular embodiment, optionally in combination with any embodiments above or below of the additive of the invention, the percentage by weight of oleanolic acid is from 2.0% to 6.0% w/w, the percentages in relation with the total weight of the additive.

In a particular embodiment of this first aspect of the invention, the additive comprises a percentage by weight of hydroxytyrosol from 0.3% to 1.8% w/w, a percentage by weight of maslinic acid from 2.0% to 9.5% w/w, and a percentage by weight of oleanolic acid from 0.5% to 3.5% w/w, all percentages in relation with the total weight of the additive. In even a more particular embodiment, in the additive the percentage by weight of hydroxytyrosol is 0.3% w/w, the percentage by weight of maslinic acid is 2.0% w/w, and the percentage by weight of oleanolic acid is 1.0% w/w, all percentages in relation with the total weight of the additive.

In another particular embodiment of the first aspect, the percentage by weight of hydroxytyrosol is from 2.5% to 5.0%, the percentage by weight of maslinic acid is from 12.5% to 20.0% w/w, and the percentage by weight of oleanolic acid is from 5.0% to 15% w/w, all percentages in relation with the total weight of the additive.

This additive comprising the three ingredients in the indicated percentages or proportions is conceived as a composition helping nutrition of animals in sensitive stages of their lives (i.e., young animals), since it promotes intestine maturity.

In yet another more particular embodiment, the additive for feed comprises hydroxytyrosol, maslinic acid, and oleanolic acid, and wherein the amounts in percentage by weight of the compounds HT/MA/OA are selected from the combinations consisting of: 2.6%/9.9%/2.3%, 2.3%/11.4%/4.2%, 2.1%/11.6%/3.6%, 1.0%/5.7%/2.6%, 0.8%/3.9%/1.8%, 0.9%/3.6%/1.8%, 2.2%/10.8%/4.1%, 1.0%/5.8%/2.7%, 0.36%/2.76%/1.10%, and 0.3%/2.0%/1.0%, all percentages in relation with the total weight of the additive.

These weight percentages of the ingredients in the additive, allow the ranges of desired ratios of weights proved to be effective, namely a ratio of the weight of MA and of HT from 2 to 20 and a ratio of the weight of MA and of OA from 1 to 10. These ratios are maintained in the final feedstuff where the additives are mixed or slightly changed in case the feed already contains certain amounts of HT, MA or OA. Thus, another way of defining the additives of the invention considering the amounts of the ingredients of interest therein, is by indicating the ratios between weights or percentages of the ingredients.

In a particular embodiment of the additive, the ratio of the weight of MA and of HT in the additive is from 3.3 to 10.

In another more particular embodiment, optionally in combination of any of the embodiments of the additive disclosed above or below, the ratio of the weight of MA and of OA in the additive is from 1.7 to 5.0.

In a more particular embodiment of the additive of the first aspect, the ratio of the weight of MA and of HT in the additive is 6, and the ratio of the weight of MA and of OA in the additive is 2.

In another also particular embodiment of the additive, the ratio of the weight of MA and of HT in the additive is from 2.0 to 4.0, and the ratio of the weight of MA and of OA in the additive is from 1.0 to 2.0.

In another also particular embodiment of the additive, the ratio of the weight of MA and of HT in the additive is from 6.0 to 20.0, and the ratio of the weight of MA and of OA in the additive is from 3 to 10.

In also another also particular embodiment of the additive, the ratio of the weight of MA and of HT in the additive is from 6.0 to 20.0, and the ratio of the weight of MA and of OA in the additive is from 1.0 to 2.0.

In also another also particular embodiment of the additive, the ratio of the weight of MA and of HT in the additive is from 2.0 to 4.0, and the ratio of the weight of MA and of OA in the additive is from 3 to 10.

Among the binders that can be used in the additive, the binder is selected from the group consisting of a mineral oil, petrolatum, vegetal origin oil and mixtures thereof.

Petroleum jelly, petrolatum, white petrolatum, soft paraffin, or multi-hydrocarbon, CAS number 8009-03-8, is a semi-solid mixture of hydrocarbons (with carbon numbers mainly higher than 25).

Vegetable oils, vegetal origin oils, or vegetable fats, are oils extracted from seeds, or less often, from other parts of fruits. Like animal fats, vegetable fats are mixtures of triglycerides. Soybean oil, rapeseed oil, and cocoa butter are examples of fats from seeds. In common usage, vegetable oil may refer exclusively to vegetable fats which are liquid at room temperature.

Mineral oil is any of various colourless, odourless, light mixtures of higher alkanes from a mineral source, particularly a distillate of petroleum.

In a more particular embodiment, it is vegetal origin oil. Even in a more particular embodiment is vegetal origin oil selected from soybean oil and palm-based oil. Even in another more particular embodiment, it is a vegetal oil comprising (C6-C12)-alkyl esters of glycerol. In another particular embodiment, the vegetal oil comprising (C6-C12)-alkyl esters of glycerol is a medium-chain triglyceride, comprising two or three fatty acids having an aliphatic tail of 6-12 carbon atoms. In even a more particular embodiment, the binder is a medium-chain triglyceride, wherein the fatty acids are selected from caprylic acid (C8:0), capric acid (C10:0) and combinations thereof. In even a more particular embodiment, the binder is a triglyceride of caprylic acid and capric acid, more in particular from palm-based oil origin.

The term "(C6-C12)-alkyl" shall be construed as straight or branched. It includes, in particular, caproate, caprylate, caprate and laurate.

These additives of the invention are compositions comprising the ingredients of interest and carriers, such as mineral carriers, like sodium chloride or calcium carbonate, or vegetal carriers and products derived thereof, like maltodextrin or dextrose among others. The additives also comprise other formulation aids, comprising solid binders and anti-caking agents such as colloidal silica, silicic acid precipitated and dried or sepiolite, flavours, and preservatives such as propionic acid and its salts, acetic acid and its salts, lactic acid and its salts, sorbic acid and its salts, disulfite salts, and combinations thereof. These carriers and formulation aids together with the amounts of hydroxytyrosol, maslinic acid and oleanolic acid amount to the 100% by weight of the additive.

In another particular embodiment, the additives have a final humidity from 10% to 20%, measured using the Karl Fisher titration method.

Preparation method of the additive includes the mixture of the desired amounts of HT, MA and OA from the several sources of the ingredients. In a particular embodiment, the ingredients are in extracts of several parts of *Olea europaea* and the method comprises mixing and stabilizing these extracts to reach the desired amounts and ratios of HT, MA and OA. If extracts are liquid, they can be dried by evaporation or directly adsorbed on inner support. If extracts are solid, they can be directly mixed and stabilized to avoid segregation and/or degradation.

In a particular embodiment, the method of preparation of the additive according to the first aspect comprises:
  (a) Adding in a recipient (i.e., a tank) a source of HT to have in the final additive from 0.3% to 5.0% together with appropriate carriers;
  (b) Adding to the recipient one or more flavours and preservatives, and optionally additional carriers, and mixing for a period of time to obtain a homogeneous mixture;
  (c) Adding to the mixture of step (b) while stirring a source of MA and OA, said source in particular from an extract of *Olea europaea*, more in particular a non-ethanolic extract of *Olea europaea*, and giving a percentage by weight of MA from 2.0% to 20% w/w and a percentage by weight of OA from 0.5% to 15% w/w in the final additive.

In a particular embodiment of the method, the source of HT and of MA and OA is a liquid source, thus giving a liquid additive.

In a particular embodiment, the method of preparation of the additive in particulate form comprises:
  (a) Adsorbing a liquid source of HT comprising from 1% to 20% w/w of HT, on an inner support or carrier, in particular on silicic acid precipitated and dried;
  (b) Adding to the mixture one or more flavours and preservatives;
  (c) Adding to the mixture of step (b) a second source of HT, in particular a solid HT comprising from 4.5 to 10% w/w HT, to adjust the percentage by weight of HT in the final additive from 0.3% to 5.0% and mixing for a period of time to obtain an homogeneous mixture;
  (d) Adding to the mixture of step (c) while stirring a source of MA and OA, said source in particular from an extract of *Olea europaea*, more in particular a non-ethanolic extract of *Olea europaea*, and giving a percentage by weight of MA from 2.0% to 20% w/w and a percentage by weight of OA from 0.5% to 15% w/w in the final additive, to obtain inner support particles with adsorbed HT, MA and OA;
  (e) Adding one or more binders to mixture of step (d) and continuing mixing until homogeneity; and
  (f) Sifting the product mixture of step (e) through a 2 mm sieve to reach a particulate form with a mean particle size higher than 500 μm, and where more than 70% of the particles have a particle diameter higher than 400 μm and less than 30% of the particles have a particle diameter lower than 250 μm.

In a particular embodiment of the method of preparation of the additive of the first aspect, the liquid source of HT is also an extract of *Olea europaea*.

In another particular embodiment of the method of preparation of the additive of the first aspect, the preservatives are in particular selected from antifungal and/or antibacterial agents, as well as other specific ingredients such as flavour agents.

The additive of the invention can also be defined by its method of preparation, being an additive for domesticated animal feed comprising hydroxytyrosol, maslinic acid, and oleanolic acid, in which the percentage by weight of hydroxytyrosol is from 0.3% to 5.0%, the percentage by weight of maslinic acid is from 2.0% to 20% w/w, and the percentage by weight of oleanolic acid is from 0.5% to 15% w/w, all percentages in relation with the total weight of the additive; said additive obtainable by a method of preparation that comprises the following steps:
  (a) Adding in a recipient (i.e., a tank) a source of HT to have in the final additive from 0.3% to 5.0% together with appropriate carriers;
  (b) Adding to the recipient one or more flavours and preservatives, and optionally additional carriers, and mixing for a period of time to obtain an homogeneous mixture;
  (c) Adding to the mixture of step (b) while stirring a source of MA and OA, said source in particular from an extract of *Olea europaea*, more in particular a non-ethanolic extract of *Olea europaea*, and giving a percentage by weight of MA from 2.0% to 20% w/w and a percentage by weight of OA from 0.5% to 15% w/w in the final additive.

Thus, also the additive in particulate form (i.e., solid) of the invention can also be defined by its method of preparation, in such a way that it is an additive for domesticated animal feed, comprising hydroxytyrosol, maslinic acid, oleanolic acid and a binder, in which the percentage by weight of hydroxytyrosol is from 0.3% to 5.0%, the percentage by weight of maslinic acid is from 2.0% to 20% w/w, and the percentage by weight of oleanolic acid is from 0.5% to 15% w/w, all percentages in relation with the total weight of the additive, and wherein the additive is in particulate form with a mean particle size higher than 500 μm, and where more than 70% of the particles have a particle diameter higher than 400 μm and less than 30% of the particles have a particle diameter lower than 250 μm; said additive obtainable by a method of preparation that comprises the following steps:
  (a) Adsorbing a liquid source of HT comprising from 1% to 20% w/w of HT, on an inner support or carrier, in particular on silicic acid precipitated and dried;
  (b) Adding to the mixture one or more flavours and preservatives;
  (c) Adding to the mixture of step (b) a second source of HT, in particular a solid HT comprising from 4.5 to 10% w/w HT, to adjust the percentage by weight of HT in the final additive from 0.3% to 5.0% and mixing for a period of time to obtain an homogeneous mixture;
  (d) Adding to the mixture of step (c) while stirring a source of MA and OA, said source in particular from an extract of *Olea europaea*, more in particular a non-ethanolic extract of *Olea europaea*, and giving a percentage by weight of MA from 2.0% to 20% w/w and a percentage by weight of OA from 0.5% to 15% w/w in the final additive, to obtain inner support particles with adsorbed HT, MA and OA;
  (e) Adding one or more binders to mixture of step (d) and continuing mixing until homogeneity; and
  (f) Sifting the product mixture of step (e) through a 2 mm sieve to reach a particulate form with a mean particle size higher than 500 μm, and where more than 70% of the particles have a particle diameter higher than 400 μm and less than 30% of the particles have a particle diameter lower than 250 μm.

Invention also encompasses as a second aspect an additivated feedstuff (animal feed), ready for use, comprising the additive as defined in the first aspect, wherein the ratio of the weight of maslinic acid and of hydroxytyrosol (MA/HT) in the final feedstuff is from 2 to 20 and the ratio of the weight of maslinic acid and of oleanolic acid (MA/HT) in the final feedstuff is from 1 to 10, being weight or amount of hydroxytyrosol, maslinic acid and oleanolic determined by LC-MS.

In a particular embodiment of the second aspect, the ratio of the weight of maslinic acid and of hydroxytyrosol (MA/HT) in the final feedstuff is from 3.3 to 10.

In another particular embodiment of the additivated feedstuff, the ratio of the weight of maslinic acid and of oleanolic acid (MA/OA) in the final feedstuff is from 1.7 to 5.0.

In another particular embodiment of the additivated feedstuff according to the invention, the ratio of the weight of maslinic acid and of hydroxytyrosol (MA/HT) in the final feedstuff is from 2.0 to 4.0, and the ratio of the weight of the ratio of the weight of maslinic acid and of oleanolic acid (MA/OA) in the final feedstuff is from 1.0 to 2.0.

In another particular embodiment of the additivated feedstuff according to the invention, the ratio of the weight of maslinic acid and of hydroxytyrosol (MA/HT) in the final feedstuff is from 6.0 to 20.0, and the ratio of the weight of the ratio of the weight of maslinic acid and of oleanolic acid (MA/OA) in the final feedstuff is from 1.0 to 2.0.

In another particular embodiment of the additivated feedstuff according to the invention, the ratio of the weight of MA and of HT in the final feedstuff is from 6.0 to 20.0, and the ratio of the weight of MA and of OA in the final feedstuff is from 3 to 10.

In another particular embodiment of the additivated feedstuff according to the invention, the ratio of the weight of MA and of HT in the final feedstuff is from 2.0 to 4.0, and the ratio of the weight of MA and of OA in the final feedstuff is from 3 to 10.

In a particular embodiment, optionally in combination with any embodiment above or below of the additivated feedstuff, the additivated feedstuff comprises HT at a concentration (mass ratio) from 2.5 ppm to 20 ppm. In yet another more particular embodiment HT concentration is from 5.0 ppm to 10.0 ppm. More in particular the concentration of HT in the final feed is selected from 2.5, 3.0, 4.0, 5.0, 6.0, 7.0, 8.0, 9.0, 10.0, 11.0, 12.0, 13.0, 14.0, 15.0, 16.0, 17.0, 18.0, 19.0, and 20.0 ppm.

In another particular embodiment, optionally in combination with any embodiment above or below of the additivated feedstuff, it comprises MA at a concentration (mass ratio) from 10 ppm to 75 ppm. More in particular the concentration of MA is from 25 ppm to 60 ppm. More in particular the concentration of MA is selected from 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 51.0, 52.0, 53.0, 54.0, 55.0, 56.0, 57.0, 58.0, 59.0, 60.0, 61.0, 62.0, 63.0, 64.0, 65.0, 66.0, 67.0, 68.0, 69.0, 70.0, 71.0, 72.0, 73.0, 74.0, and 75.0 ppm.

In another particular embodiment, optionally in combination with any embodiment above or below of the additivated feedstuff, it comprises OA at a concentration (mass ratio) from 5 ppm to 35 ppm. More in particular the concentration of OA is from 10.0 ppm to 20.0 ppm. More in particular the concentration of OA is selected from 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, and 35.0 ppm.

In another particular embodiment of the second aspect, in the ready to use feed for the domestic animal, the concentration of HT is of at least 2.5 ppm and up to 20 ppm, the concentration of MA is of at least 10 ppm and up to 75 ppm, and the concentration of OA is of at least 5 ppm and up to 35 ppm. In another particular embodiment, in the final feed for the domesticated animal, the concentration of HT is of at least 5 ppm and up to 10 ppm, the concentration of MA is of at least 25 ppm and up to 60, and the concentration of OA is of at least 10 ppm and up to 20 ppm. In yet a more particular embodiment of the combined used of the invention, the concentration in the final feed of HT is of 10 ppm, the concentration of MA is of 60 ppm, and the concentration of OA is of at 20 ppm.

In another particular embodiment of the additivated feedstuff according to the second aspect, the total amount or concentration of the additive in the final feedstuff is that that allows in the final feedstuff the previously indicated ranges of concentrations (in ppm) of any of HT, MA and OA. Thus, the amount, allowing in particular in the final feedstuff the concentration of HT of at least 2.5 ppm and up to 20 ppm, the concentration of MA of at least 10 ppm and up to 75 ppm, and the concentration of OA of at least 5 ppm and up to 35 ppm.

Thus, the additivated feedstuff of the invention is the one comprising the additive as defined in the first aspect, wherein in the feedstuff the ratio of the weight of maslinic acid and of hydroxytyrosol (MA/HT) in the final feedstuff is from 2 to 20 and the ratio of the weight of maslinic acid and of oleanolic acid (MA/OA) in the final feedstuff is from 1 to 10, and wherein further:

(a) the feedstuff comprises an amount of the said additive giving HT at a concentration from 2.5 ppm to 20 ppm, MA at a concentration of at least 10 ppm and up to 75 ppm, and a concentration of OA of at least 5 ppm and up to 35 ppm, all concentrations in relation to the total weight of the feedstuff; or alternatively (b) the feedstuff comprises the additive which comprises a binder and it is in particulate form with a mean particle size higher than 500 μm, and where more than 70% of the particles have a particle diameter higher than 400 μm and less than 30% of the particles have a particle diameter lower than 250 μm; or alternatively (c) the feedstuff comprises an amount of additive giving HT at a concentration from 2.5 ppm to 20 ppm, MA at a concentration of at least 10 ppm and up to 75 ppm, and a concentration of OA of at least 5 ppm and up to 35 ppm, all concentrations in relation to the total weight of the feedstuff, and said additive comprises a binder and it is in particulate form with a mean particle size higher than 500 μm, and where more than 70% of the particles have a particle diameter higher than 400 μm and less than 30% of the particles have a particle diameter lower than 250 μm.

The skilled person will know how to calculate the adequate amount of total additive to be added in the feedstuff, departing from the known particular percentage by weight of each of the ingredients in the said additive, and which for the hydroxytyrosol will be from 0.3% to 5.0% in the said additive, for the maslinic acid will be from 2.0% to 20% w/w in the additive, and for the oleanolic acid will be from 0.5% to 15% w/w in the additive.

As will be depicted in examples below, the additive with the above-indicated percentages by weight in combination of the hydroxytyrosol, the maslinic acid and the oleanolic acid, allow the addition in the final feedstuff of a wide range of amounts from 250 to 3000 ppms of additive in the final feedstuff, while providing the particular working concentrations (i.e., ppm) of each of the ingredients hydroxytyrosol, the maslinic acid and the oleanolic acid, previously listed.

These amounts of the total additive in the feedstuff, allowed the selected ranges of concentrations of each of the ingredients, that gave good results in very young animals as will be illustrated in the examples below.

As will be depicted in Examples below, these final concentrations of the additive in the feedstuff, providing the previously indicated particular amounts of each of HT, MA and OA surprisingly promoted the productivity in the very young animals. This was due to the combination non-affecting the consumption of feedstuff, which is of relevance because consumption at early stages of life is critical. This is so, since through the feedstuff myriad of protective compounds (antibiotics, probiotics, etc.) are also provided to these animals. Thus, a non-adequate consumption of feedstuff can lead animals to death or to be more prone to disease, affecting so the final productivity.

In a particular example, the amount of the additive of the first aspect in the final feedstuff is of at least 400 ppm, and the total of the additivated feedstuff comprises HT at a concentration (mass ratio) from 2.5 ppm to 20 ppm, MA at a concentration of at least 10 ppm and up to 75 ppm, and a concentration of OA of at least 5 ppm and up to 35 ppm.

In yet another particular embodiment of the additivated feedstuff, the amount or concentration of the additive in the final feedstuff is of at least 400 ppm, this concentration of additive providing to the feedstuff, a concentration of HT of at least 2.5 ppm and up to 20 ppm, more in particular of at least 5 ppm and up to 10 ppm; a concentration of MA of at least 10 ppm and up to 75 ppm, more in particular of at least 25 ppm and up to 60; and a concentration of OA of at least 5 ppm and up to 35 ppm, more in particular of at least 10 ppm and up to 20 ppm; and wherein the ratio of MA/HT is from 3.3 to 10 and the ratio of MA/OA is from 1.7 to 5.0.

In another particular embodiment of the additivated feedstuff or feed for domesticated animals, it is feed for pigs and it is selected from the group consisting of a creep-feeding feed, prestarter diet feed, and starter diet feed, according to nomenclature of cycle of production in swine.

In another particular embodiment of the additivated feedstuff or feed for domesticated animals, it is feed for poultry, and it is selected from the group consisting of a starter diet feed, and a grower feed according to nomenclature of cycle of production in poultry.

Common feedstuff for creep-feeding in pigs is defined as a mixture comprising corn, soybean and/or wheat meal, molasses, limestone, mixtures of salts and vitamins, oils. Examples of more particular compositions include corn (about 30% w/w), wheat (20% w/w), oats (about 9% w/w), soy (about 19% w/w), lactose (about 8% w/w), calcium carbonate (about 0.7% w/w), phosphates (about 1.1% w/w), mineral salt (about 0.4% w/w), DL-methionine (about 0.3% w/w), L-Lysine (about 0.7% w/w), L-Threonine (about 0.3% w/w), L-Tryptophan (about 0.09% w/w), L-Valine (about 0.18% w/w), soy oil (about 1.1% w/w), acids (about 0.2% w/w), vitamins and trace elements (about 4 g/Kg).

Common prestarter pig diets include corn, wheat, oats, soy, sweet serums, antibiotics, mixtures of salts, and oils. A more specified model of prestarter pig diet includes corn (about 30% w/w), wheat (18% w/w), oats (about 16% w/w), soy (about 17% w/w), sweet serum (about 8% w/w), calcium carbonate (about 0.7% w/w), zinc oxide (about 0.2% w/w), phosphates (about 0.8% w/w), mineral salt (about 0.4% w/w), DL-methionine (about 0.3% w/w), L-Lysine (about 0.7% w/w), L-Threonine (about 0.3% w/w), L-Tryptophan (about 0.06% w/w), L-Valine (about 0.18% w/w), soy oil (about 1.8% w/w), acids (about 0.2% w/w), vitamins and trace elements (about 4 g/Kg).

Common starter pig diets include similar compounds, and in a more specified model of starter pig diet includes corn (about 25% w/w), wheat (25% w/w), oats (about 21% w/w), soy (about 18% w/w), calcium carbonate (about 0.8% w/w), phosphates (about 0.7% w/w), mineral salt (about 0.4% w/w), DL-methionine (about 0.2% w/w), L-Lysine (about 0.7% w/w), L-Threonine (about 0.3% w/w), L-Tryptophan (about 0.06% w/w), L-Valine (about 0.18% w/w), soy oil (about 2.5% w/w), acids (about 0.2% w/w), vitamins and trace elements (about 4 g/Kg).

The skilled animal nutritionist will know that different compositions are available in the market, and that certain compounds can be substituted by others of the same category.

In poultry, typical starter diet, and grower diets include the following (first value is % by weight in starter and second value is % by weight of grower diet): corn (about 61%/about 64%), soybean meal (about 34%/about 30%), soy oil (about 1.1%/about 2.02%), Limestone (about 1.1%/about 1.0%), dicalcium phosphate (about 1.1%/about 0.9%), salt (about 0.4%/about 0.4%), DL-methionine (about 0.3%/about 0.3%), L-lysine (about 0.2%/about 0.2%), L-threonine (about 0.08%/about 0.07%), inert filler (about 0.2%/about 0.2%), vitamins and trace elements (about 0.2%/about 0.2%), choline at 60% (about 0.05%/about 0.05%), and phosphates (about 0.03%/about 0.03%)

In the examples below all these diet types are mentioned, and they are to be understood as containing these listed ingredients or any minor variations depending on suppliers. In any case, any effect due to the composition of feedstuff (diet) is cancelled because all animals in the example in question received the same feedstuff or sequence of feedstuffs.

Thus, the additivated feedstuff comprises the particular ingredients according to the feedstuff category and the above-indicated ratios of HT, MA and OA.

Common methods of obtaining feedstuffs are known in the art. In a generic mode all include the mixture of all the ingredients in a hopper (in wet or dry mode), the optional drying to get a final humidity degree, an optional milling, and pelletization of the milled mixture to obtain granules or pellets of appropriate sizes for the animal to be fed with. In certain methods also a final treatment of hygienization of the pellets or granules is included As indicated above, the additive or the additivated feedstuff of present invention allow the combined use of hydroxytyrosol (HT), maslinic acid (MA) and oleanolic acid (OA).

Another aspect of the invention is the use of an additive as defined in the first aspect, or of an additivated feedstuff as defined in the second aspect, in a feed for a domesticated animal.

In a particular embodiment of the said use, the feed is for a domesticated animal at a non-reproductive age, thus a young non-reproductive domesticated animal, or simply a non-reproductive domesticated animal, which means it is an animal still non-sexually developed to procreate.

In particular, the domesticated animals are livestock animals, including calves, sheep, goats, pigs or poultry. In another more particular embodiment, domesticated animals are selected from the group consisting of pigs and poultry. In the particular case of poultry, they are broilers and turkeys.

This description discloses thus, for the first time, the combined use of hydroxytyrosol (HT), maslinic acid (MA) and oleanolic acid (OA) as an additive in the feeding of a domesticated animal, which domesticated animal is a mammal at birth and/or at weaning prior to the known as rearing phase.

In a particular embodiment of the said combined use, or of the use of an additive as defined in the first aspect, or of an additivated feedstuff as defined in the second aspect, it is a use in a feed for a piglet and/or a weaner. Thus, the use in the feeding of a piglet and/or a weaner.

Thus, in a more particular embodiment of this use, it is for a piglet or weaner from birth to 10 weeks after birth.

In even a more particular embodiment, it is a piglet of an initial weight from around 700 g to 2100 g at birth, and from around 3000 g to 10000 g at weaning.

In another more particular embodiment, the combined use of the three ingredients, or the use of the additive or of the additivated feedstuff as above disclosed, is in the feeding of a piglet of an initial weight from 500 g to 2500 g at birth, and from around 3000 g to 10000 g at weaning.

In the particular case of piglets and/or weaners, and in a particular embodiment of the combined used proposed (additive or feedstuff), it is for an animal receiving a diet selected from creep-feeding, and/or a prestarter diet, and/or a starter diet.

In the particular case of piglets and/or weaners, the use of the additive of the first aspect or of the additivated feedstuff of the second aspect is carried out, in a particular embodiment, with a schedule of administration comprising:

administering HT, MA and OA from birth, or from weaning prior to initiating a rearing diet.

In even a more particular embodiment of the scheduled use, during the growing of the piglets and/or weaners and prior to initiating the rearing diet, there is one or more diet change, which means that animals are challenged with a change of the diet (i.e., of type of feed). If the additive or additivated feedstuff is used, the previously commented effects on performance, weight gain and protection to diseases is enhanced in relation with the non-use of the additive or additivated feedstuffs of the invention when this diet change takes place.

The three ingredients of interest have been tested in combination in different genetic line background of pigs. In a particular embodiment the pigs are from crossbred genetic lines called DanBred×Pietrain, DanBred×Duroc, (Large-White×Landrace)×Pietrain.

Another aspect of the invention is the use of an additive as defined in the first aspect, or of an additivated feedstuff as defined in the second aspect, in a feed for a broiler from hatch to 35 days post-hatch. Thus, the use in the feeding of a broiler from hatch to 35 days post-hatch.

Another aspect of the invention is the use of an additive as defined in the first aspect, or of an additivated feedstuff as defined in the second aspect, in a feed for a turkey from hatch to 84 days post-hatch. Thus, the use in the feeding of a turkey from hatch to 84 days post-hatch.

In another more particular embodiment, the use of the additive or of the additivated feedstuff is in the feeding of a broiler of an initial weight around 40 g after hatch, and from around 2000 g to 4000 g at 35 days of life.

In another more particular embodiment, the use of the additive or of the additivated feedstuff is in the feeding of a turkey of an initial weight around 60 g after hatch, and from around 6000 g to 16000 g at 14-18 wk of life.

These animals of low initial weight are very sensitive to diseases and, moreover, tend to eat even lower amounts of feed than their littermates. With the combined use of HT, MA and OA in their diet, final weights higher than the usual ones are achieved for these kinds of animals in case of survival.

In the particular case of poultry (i.e., broilers or turkeys), the use of the additive of the first aspect or of the additivated feedstuff of the second aspect is carried out, in a particular embodiment, with a schedule of administration comprising:

administering from hatch to all along a growing phase (i.e., starter and grower phase), wherein said growing phase comprises one or more change of the diet, and prior to initiating a fattening diet.

As indicated for piglets and weaners, this schedule with the additional challenge of a change of diet (i.e., creep-feed to prestarter or prestarter to starter) did not alter the previously commented effects on performance, weight gain and protection to diseases, which were enhanced in relation with the non-use of the additive or additivated feedstuffs of the invention.

As previously commented, the ratio of the weight of MA and of HT from 2 to 20 and the ratio of the weight of MA and of OA from 1 to 10 in the feed for the domesticated animals gave the advantageous result of a proper intake of feed in animals that are considered poor consumers, in particular those at birth phase diets (i.e., creep-feeding) and/or when they are receiving first diets (i.e. prestarter or starter diets). This is a real advantage because animals acquire intestinal maturity and thus, protection against intestinal disturbances that compromise animal welfare at an early age. Particular ratios of the weight of MA and of HT are from 3.3 to 10. Particular ratios of the weight of MA and of OA are from 1.7 to 5.0.

Particular concentrations of MA are of at least 10 ppm and up to 75 ppm.

Particular concentrations of OA are of at least 5 ppm and up to 35 ppm.

Particular concentrations of the three ingredients used in combination in the feed for the domesticated animal are of HT of at least 2.5 ppm and up to 10 ppm, of MA of at least 10 ppm and up to 75 ppm, and of OA is of at least 5 ppm and up to 20 ppm. More in particular when used in combination in the final feed for the domesticated animal, the concentration of HT is of at least 5 ppm and up to 10 ppm, the concentration of MA is of at least 25 ppm and up to 60, and the concentration of OA is of at least 10 ppm and up to 20 ppm.

As above indicated MA is used as additive in feed, but it has also been reported as influencing feed intake, by reducing the said intake as demonstrated in gilthead sea bream (See Rufino-Palomares, E. E. et al. Maslinic acid, a natural triterpene, and ration size increased growth and protein turnover of white muscle in gilthead sea bream (*Sparus aurata*). Aquac. Nutr. 18, 568-580 (2012). This known drawback associated generally to triterpenes in feed was overcome with the proposed combination of HT, MA and OA at the defined ratios and concentrations (i.e., the additive comprising these ingredients or an additivated feedstuff with the said additive). This combination promoted intake of feed by these animals at very sensitive stages of their lives. As will be depicted in examples below the three ingredients HT, MA and OA were needed to increase intake of feed. According to inventor's knowledge this is the first time this ternary combination is associated to the effect of avoiding reduction of feed intake in very young domesticated animals at phase diets including one or more of the birth phase diets and the growing phase diets (i.e. creep-feeding, prestarter or starter diets in mammals, or starter diets grower diets in birds as broilers or turkey).

HT, MA and OA can be obtained in several grades of purity (purity grades), since they are synthesized or purified from the plants producing them, mainly from *Olea euro-paea*. For this reason, another source of any of them includes highly standardized extracts of olive fruit, olive leaves and other parts of the commonly known olive tree.

Thus, in another particular embodiment, optionally in combination with any of the embodiments of the additive, additivated feedstuff or their use in domesticated animal feeding, the source of HT, MA and OA is an extract of *Olea europaea*. In even a more particular embodiment, the extract is an olive fruit extract and/or an *Olea europaea* leaf extract.

Examples of extracts derived from *Olea europaea* used herein to get the particular effective amounts of the three ingredients contain, among other compounds, MA (3% to 80% w/w), HT (1% to 20% w/w), and OA (1% to 40% w/w). Other examples of extracts derived from *Olea europaea* are disclosed in the international patent application of publication WO2007/096446, in which a concentrated extract from waste material of olive oil preparation is disclosed containing, among other compounds, MA (42% to 80% w/w), HT (8% to 20% w/w), tyrosol (2% to 6% w/w), and OA (7% to 13% w/w). Extracts in WO2007/096446 are disclosed as pronutrients for improving conversion index and fat in the muscle fiber of rearing pigs. They are also proposed for improving conversion index in poultry (undetermined stage of life).

Although phase diets prior to rearing or finishing phase diets, (i.e., in pigs creep-feeding, prestarter and starter diets) are usually bought by breeder because they are really very specialized compositions, some breeders or farmers are confident with a particular starter or prestarter feed and they prefer supplementing their own choice with the amounts of vitamins, antibiotics, probiotics, prebiotic and other additives according to nutritionists and/or veterinarian prescriptions.

For this reason, the additives of the first aspect suppose a contribution to the field, allowing the breeders to accommodate their usually employed feedstuffs with the additive.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

Examples

Example 1. HT, MA and OE Stabilize Activated Mastocytes and Improve Intestinal Barrier and Nutrient Transport In Vitro In vitro assays performed on mast cells using several mixtures including HT, MA and OA, revealed that the extracts mixtures could display mast stabilizing activity in LAD2 cells (human mastocytes) in immunological and non-immunological conditions. Stability was related to stabilization of activated mastocytes rather than the suppression of activation (i.e., degranulation was avoided but mastocytes were activated). In RBL-2H3 cells (rat "mastocytes like") activity was also displayed in non-immunological conditions.

Immunological condition means that cells were challenged with doses of immunoglobulin E (IgE-stv), related to allergic responses. Non-immunologic conditions means that cells were challenged with substance P (SP) in LAD2 cells (a compound used to promote activation of immune system) and with an ionophore (opening of Ca2+channel) in RBL-2H3 cells.

Tested compounds included:

Control (DMSO), Cromolyn (100 μM), a mixture of pure compounds at weight ratio HT:MA:OA 14:50:12 (100 μg/mL), formulation A with HT:MA:OA at ratio 9:50:23 (100 μg/mL) and formulation B with HT:MA:OA at ratio 8:50:23 (100 μg/mL).

Figure 2:
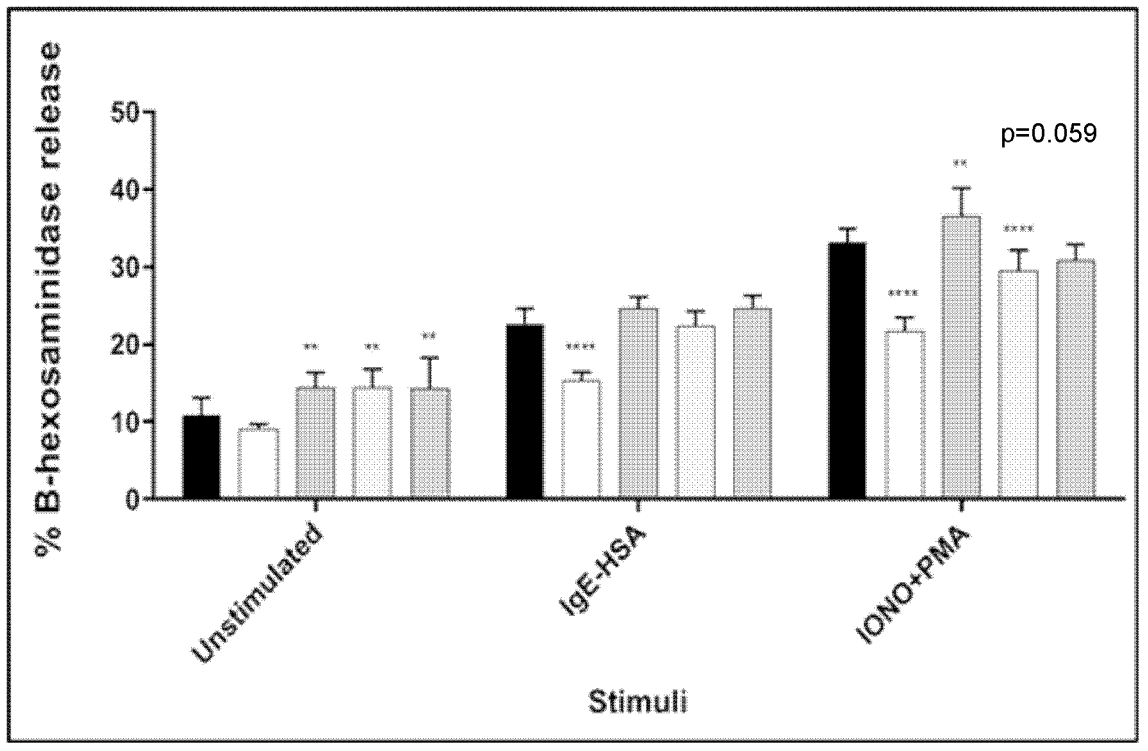
FIG. 2 shows the percentage of CD63 positive cells for RBL-2H3 cells, also submitted to different stimuli: unstimulated; challenged with doses of inmunoglobulin E (IgE-stv), related to allergic responses; and challenged with an ionophore (IONO-PMA). Control (DMSO), left bar in each set, Cromolyn (100 µM) second bar in the set, a mixture of pure compounds at weight ratio HT:MA:OA 14:50:12 (100 µg/mL) as the third bar in each set, formulation A with HT:MA:OA at ratio 9:50:23 (100 µg/mL) and formulation B with HT:MA:OA at ratio 8:50:23 (100 µg/mL), represented respectively by the fourth and fifth bars in each set

Data are depicted in FIG. 1 and FIG. 2, where % of B-hexosaminidase release (FIG. 1A) and the percentage of CD63 positive cells (FIG. 1B) are disclosed for LAD2 cells, and the % of B-hexosaminidase release is disclosed for RBL-2H3 cells (FIG. 2).

Assays commonly used to determine mast cells degranulation ($\beta$-hexosaminidase activity and CD63 determination by flow cytometry) were carried out in two cell models: i) the LAD2 cell line and ii) the RBL-2H3 cell line. Cells were stimulated by immune and non-immune stimuli. For the immunological stimuli (IgE-dependent activation) it was proceed as follows: On the first day, cells were sensitized overnight with biotinylated IgE (LAD2) or anti-DNP IgE (RBL-2H3). On day two, the products were added and the cells stimulated with streptavidin or DNP-HSA to induce IgE crosslinking. As a non-immunological stimuli for degranulation, mast cells were incubated with substance P (LAD2) or with Ionomycin and PMA (RBL-2H3) adding the products. Cromolyn, a mast cell stabilizer, was used as a control.

As can be seen, incubation with the products of LAD2 cells didn't significantly decrease the precentage of CD63 positive cells (activated mastocytes). However, the activity of released $\beta$-hexoxaminidase in the media after both immunological and non-immunological activation of mastocytes was clearly diminished. These results demonstrate the capacity of the products to prevent the degranulation of activated mastocytes in similar extent than positive control Cromolyn.

Incubation of RBL-2H3 cell line with products didn't display any effect under immunological stimuli. On the other hand, while the mixture of pure compounds increased $\beta$-hexoxaminidase activity in the media under non-immunological stimulation, both formulations clearly decreased its activity, indicating a prevention of mastocytes degranulation with the extracts mixture.

Formulation C with HT:MA:OA at weight ratio 11:50:23 (50 μg/mL) and formulation D with HT:MA:OA at weight ratio 12:50:15 (50 μg/mL) were also tested on a cell line of pig enterocytes (IPEC-J2), at different conditions. IPEC-J2 cells were seeded into a permeable transwells membrane insert (6.5 mm diameter, 0.4 μm pore size, 0.33 cm2, polyester, Costar) at $1\times10^5$ cells/cm$^2$ to form a confluent monolayer within 4 days. Medium was replaced 48 h post-seeded and products were added on the apical side. On day 3 post-seeded, cells were treated with LPS (50 ng/mL) on the apical side and 24 h post-LPS stimulation epithelial cell integrity was assessed through the measurement of trans-epithelial electrical resistance (TEER) using a Milli-cell ERS-2 Voltohmmeter (Millipore, Billerica, MA). For each condition, triplicates were carried out in three independent experiments. At the end of incubation apical and basal media were eliminated and RNAlater solution (1 mL/well) was added to the cells for RNA stabilization and storage. Total RNA was extracted using RNA Mini Kit columns from Ambion (Life technologies, Carlsbad, CA) and stored at −80° C. for subsequent retrotranscription and quantitative RT-PCR. The extraction of total RNA was carried out using PureLink™ RNA Mini Kit according to the manufacturer's protocol. Total ARN (1 μg) was transcripted using the High-Capacity cDNA Reverser Transcription kit (Applied Biosystem, USA) in a 20 μL final volume following suppliers instructions. RT-PCR were performed in a StepOne Plus system (Applied Byosistems, EE. UU.) using specific primers (Isogen, Holand) and the Fast SYBR Green Master Mix (Applied Biosystems, USA). Ct data was normalized against β-actin y GAPDH and relative expression expressed compared by the $2^{-\Delta\Delta Ct}$ methodology.

Data on TEER (related with cell proliferation), gene expression of CDH1, OCLDN and CLDN4 (related with improved intestinal barrier performance), gene expression of IL8, GPx1 and CAT (related with inflammation and oxidative stress) and gene expression of ATB0 (related with nutrient transport) are depicted in Table 1 below. As can be seen, both formulations prevent the negative effects associated with the application of LPS to the cell monolayer in markers associated with barrier integrity (TEER, CDH1, OCLDN, CLDN4), inflammation (IL-8), oxidative stress (GPx1, CAT) and nutrient transport (ATB0).

TABLE 1

| data on IPEC-J2 | | | | | | | | |
|---|---|---|---|---|---|---|---|---|
| Sample | TEER | CDH1 | OCLDN | CLDN4 | IL8 | GP × 1 | CAT | ATB0 |
| Control | 100 | 0.98 | 1.04 | 1.02 | 0.55 | 0.81 | 1.11 | 1.02 |
| LPS | 61.7 | 1.00 | 1.00 | 1.00 | 1.00 | 1.00 | 1.00 | 1.00 |
| Formulation C | 136.5 | 1.19 | 1.15 | 1.13 | 0.53 | 1.30 | 1.34 | 1.35 |
| Formulation C + LPS | 115.8 | 1.22 | 1.13 | 1.07 | 0.87 | 1.41 | 1.29 | 1.37 |
| Formulation D | 135.6 | 1.32 | 1.27 | 1.14 | 0.52 | 1.34 | 1.48 | 1.35 |
| Formulation D + LPS | 126.3 | 1.42 | 1.18 | 1.20 | 0.86 | 1.45 | 1.28 | 1.24 |
| Genistein | 129.3 | | | | | | | |
| Genistein + LPS | 106.6 | | | | | | | |

Control: DMSO;

LPS: lipopolysaccharide (Sigma);

Genistein (50 μM, Sigma) positive control;

TEER: transepithelial electrical resistance measured as $\Omega/cm^2$;

CDH1: epithelial cadherin 1;

OCLDN: occludin;

CLDN4: claudin 4;

IL8: interleukine-8;

GP × 1: glutathione peroxidase 1;

CAT: catalase;

ATB0: Na$^+$-dependent amino acid transporter.

Example 2. Assay in Weaners. Test of Social Stress Challenge

In this assay, transition weaners until 63 days of life were submitted to social stress (change of penmates).

After weaning (day=0) weaners were divided in 3 different groups: I) (C−) receiving a creep-feed (day 0 to 6), prestarter diet (day 7 to 21) and a starter diet (days 22 to 42); II) (C+) same diets as control but submitted to social stress; III) (T) same diets supplemented with formulation F (2500 ppm of a composition containing 0.36% w/w of HT, 2.76% w/w of MA and 1.10% w/w of OA) and also submitted to social stress. Final ratios of detected amounts of MA and HT (MA/HT) and of amounts of MA and OA (MA/OA) were, respectively, 7.7 and 2.5.

Social stress was further inferred (days 22 to 24) by changing weaners already adapted to their penmates to unfamiliar pens and weaners belonging to the same experimental group (C+vs T). Sampling of jejunum and ileum was carried out (days 25 and 26) and the assay ended at day 42.

Mast cells measurements were performed in the jejunum and ileum, with a light microscope (BHS, Olympus, Barcelona, Spain). The number of mast cells (total and degranulated) in the *lamina propia* was determined by counting Toluidine blue positive cells in an area of 40.000 μm2 from each section using a grid ocular (Olympus, Microplanet). Measurements were taken in 10 areas from each animal. All the morphometric analyses were conducted by the same person, who was blinded to the treatments. Data in Table 2 show the number of degranulated mast cell in the jejunum and in ileum for the three groups: (C−) weaners with control diet; (C+) weaners with control diet and social stress; and (C+/T) weaners fed with formulation F and social stress.

TABLE 2

| Degranulated mast cells | | | |
|---|---|---|---|
| | C | C+ | T |
| Degranulated mast cells jejunum | | | |
| Mean | 0.4819 | 0.8650 | 0.5640 |
| Std. Deviation | 0.2935 | 0.7185 | 0.2995 |
| Std. Error of Mean | 0.08848 | 0.2074 | 0.09471 |
| Degranulated mast cells ileum | | | |
| Mean | 0.7083 | 1.056 | 0.6191 |
| Std. Deviation | 0.4735 | 0.6229 | 0.4393 |
| Std. Error of Mean | 0.1372 | 0.1798 | 0.1325 |

Data in Table 2 confirm that with the additivated diet, stress induced by social changes and viewed as number of degranulated cells was lower (similar to control; no stress). A reduction of 41.5% of the number of degranulated cells in ileum could be counted (1.06 vs 0.62), and of 35.6% in jejunum (0.87 vs 0.56).

Weaners were also assessed on terms of final BW and daily means weight gain. Final BW of stressed weaners (C+) vs. stressed weaners fed with additivated diet (C+/T) was of 19.0 vs 19.6 Kg, thus a 3.2% in increase in body weight. The daily mean gain was of 336 d/day in (C+) vs 348 d/day in (C+/T).

Example 3. Assay in Weaners. Challenge with Lipopysacharides of *E. coli* (LPS)

In a different assay, weaners from weaning (day=0) to 49 days post-weaning were challenged with increasing doses of

*E. coli* lipopolysaccharides (LPS, Sigma) intramuscularly, at days 24, 26, 28 and 30. LPS doses ranged from 40 μg/Kg BW to 48 μg/ml.

At weaning, weaners were divided in two different groups: I) (C) animals fed with control diet and challenged with LPS; II) (T) animals fed control diet supplemented with formulation G (500 ppm in final feed) including HT/MA/OA and challenged with LPS. Two different diets were offered to weaners: a prestarter diet from day 0 to day 11 and a started diet from day 12 to day 49. Formulation G consisted in a preparation containing 2.3% w/w of HT, 11.4% w/w of MA and 4.2% w/w of OA). Final ratios of detected amounts of MA and HT (MA/HT) and of amounts of MA and OA (MA/OA) were, respectively, 5.0 and 2.7.

As above indicated, ppm means parts per millions and corresponded to grams of additive per ton of animal feed.

The final BW was of 20.9 Kg (C) vs 22.0 Kg in (T). An increase of 5% BW in animals receiving the additive compared to control group was registered.

Data of this assay allow concluding that with the animal feed comprising HT, MA and OA at the indicated proportions, the recovery of animals was improved after a chronic systemic challenge exposure.

Example 4. Assay in Weaners. Comparison with Medicated Diets

In a different assay, weaners from weaning (day=0) to 42 days post-weaning were fed with diets with and without medication. At weaning, weaners were divided in three different groups: I) (C) animals fed with control diet; II) (AMA) animals fed with control diet supplemented with antimicrobials and III) (T) animals fed control diet supplemented with formulation G (500 ppm in final feed) including HT/MA/OA. Two different diets were offered to weaners: a prestarter diet from day 0 to day 14 and a started diet from day 15 to day 42. Formulation G consisted in a preparation containing 2.3% w/w of HT, 11.4% w/w of MA and 4.2% w/w of OA). Final ratios of detected amounts of MA and HT (MA/HT) and of amounts of MA and OA (MA/OA) were, respectively, 5.0 and 2.7. Antimicrobials in group (AMA) included amoxicillin (300 ppm) and ZnO (2500 ppm) in prestarter diet and amoxicillin (300 ppm) in starter diet.

As above indicated, ppm means parts per millions and corresponded to grams of additive per ton of animal feed The final BW was of 20.9 Kg (C), 21.1 (AMA) and 21.7 in (T). An increase of 4% in final BW of animals receiving the additive compared to control group was registered. Furthermore, an increment of 3% compared to medicated group was also registered.

Figure 3:
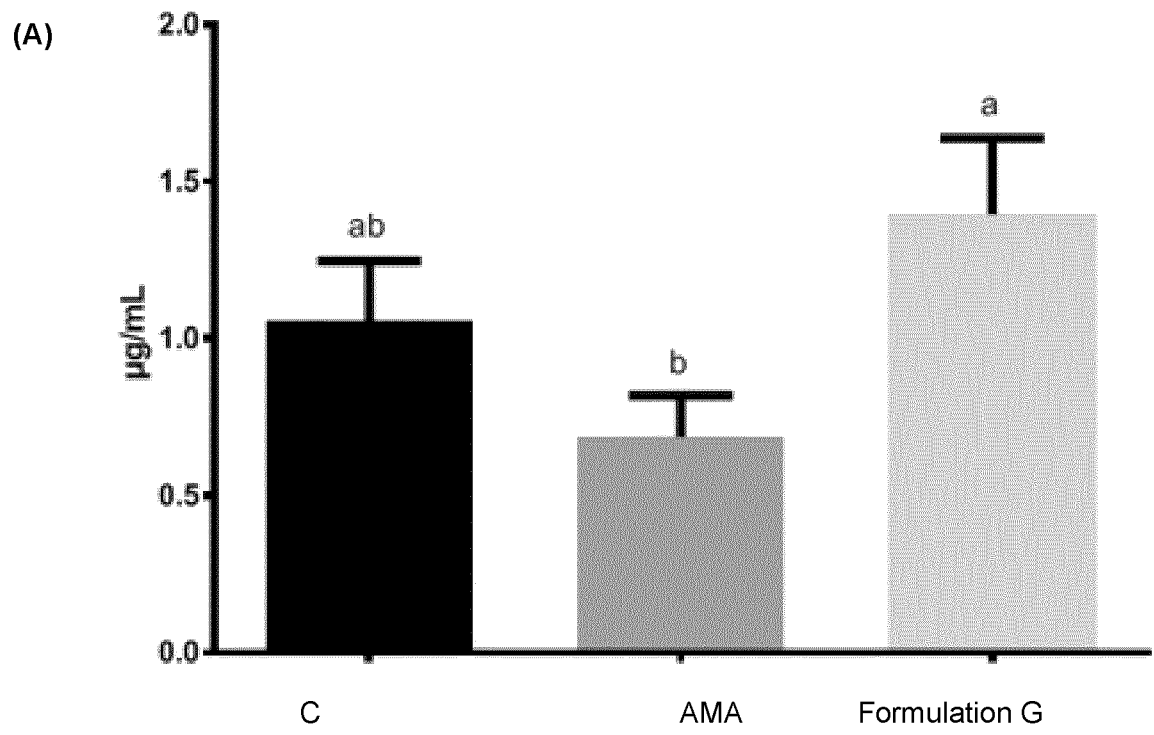
FIG. 3 is a graphic showing in (A) the levels in serum of mannitol (µg/ml), and in (B) levels of cobalt-EDTA complex (Co-EDTA in µg/L), in piglets receiving: (C) control diet; (AMA) control diet supplemented with antimicrobials and (T) control diet supplemented with 500 ppm of the formulation G (2.3% w/w of HT, 11.4% w/w of MA and 4.2% w/w of OA). Different letters means p<0.05 (uncorrected Dunn's test).
Figure 3:
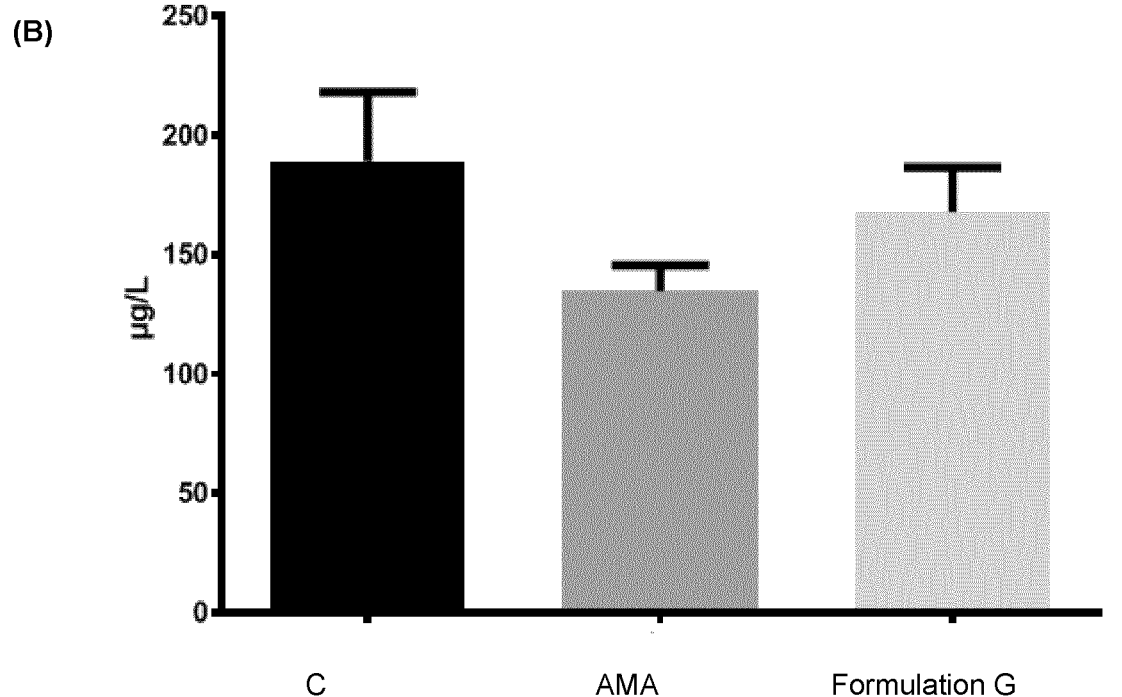

FIGS. 3(A) and (B) show, respectively, the levels in serum of mannitol and cobalt-EDTA complex (Co-EDTA) in piglets receiving: (C) control diet; (AMA) control diet supplemented with antimicrobials and (T) control diet supplemented with the formulation G.

Mannitol and Co-EDTA demonstrate that nutrient absorption was improved in the presence of additivated diet, in higher extent even than medicated diets.

Data of this assay allow concluding that with the animal feed comprising HT, MA and OA at the indicated proportions, use of antimicrobials can be reduced or even avoided maintaining or even improving performance of animals (note final BW of (AMA) vs (T) groups). Furthermore, permeability markers analysis showed an improved nutrient absorption in animals fed with formulation G supplemented diet.

Example 5. Assay in Piglets/Weaners. Challenge with Lipopolysacharides of *E. coli* (LPS) and Comparison with Medicated Diets In a different assay, piglets receiving the mixture of active ingredients from day 7 of life to day 63 were challenged with increasing doses of *E. coli* lipopolysaccharides (LPS) intramuscularly, at days 21, 23, 25 and 27. LPS doses ranged from 50 μg/Kg BW to 56 μg/ml.

At day 7 of life, lactating piglets were divided in two different groups: (A) lactating piglets with control creep-feed offered in the maternity; (B) lactating piglets with control feed supplemented with formulation H (1500 ppm) including HT/MA/OA also offered in the maternity. Formulation H consisted in a preparation containing 0.8% w/w of HT, 3.9% w/w of MA and 1.8% w/w of OA. Final ratios of detected amounts of MA and HT (MA/HT) and of amounts of MA and OA (MA/OA) were, respectively, 4.9 and 2.2.

At weaning, weaners were divided in three different groups: I) (C) animals coming from treatment A in maternity, receiving control non-medicated diets and challenged with LPS; II) (AMA) animals coming from treatment A in maternity, fed with diets supplemented with antimicrobials and challenged with LPS; Ill) (T) animals coming from treatment B in maternity, receiving feed supplemented with formulation J (1500 ppm) including HT/MA/OA and challenged with LPS. Formulation J consisted in a preparation containing 0.9% w/w of HT, 3.6% w/w of MA and 1.8% w/w of OA. Final ratios of detected amounts of MA and HT (MA/HT) and of amounts of MA and OA (MA/OA) were, respectively, 4.0 and 2.0. Weaners were fed with three different diets during their transition period: a creep-feed diet from day 7 of life to day 28, a prestarter diet from day 29 of life to day 35 and a started diet from day 36 to day 63. Medicated diets included amoxicillin (300 ppm), colistin sulphate (120 ppm) and also ZnO (2500 ppm) in creep-feed (only after weaning) and prestarter diets and amoxicillin (300 ppm) in starter diet.

As above indicated, ppm means parts per millions and corresponded to grams of additive per ton of animal feed.

Figure 4:
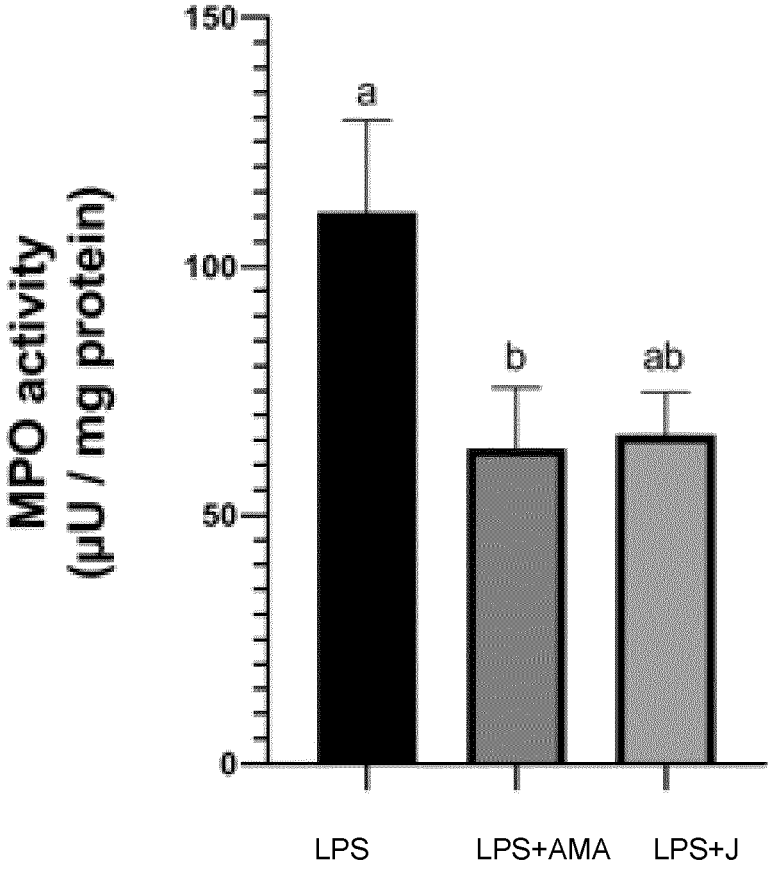
FIG. 4 shows faecal myeloperoxidase activity in μUnits/mg of total protein of piglets challenged with increasing doses of *E. coli* lipopolysaccharides (LPS). Control (LPS) are results of piglets coming from treatment A in maternity, receiving control non-medicated diets at maternity and challenged with LPS. (LPS+AMA) are results of piglets coming from treatment A in maternity, fed with diets supplemented with antimicrobials and challenged with LPS. (LPS+J) are the test (T) animals coming from treatment B in maternity, receiving feed supplemented with formulation J (1500 ppm) including HT/MA/OA and challenged with LPS. Formulation J consisted in a preparation containing 0.9% w/w of HT, 3.6% w/w of MA and 1.8% w/w of OA. Different letters means p<0.05 (uncorrected Dunn's test).

Faecal myeloperoxidase (MPO) activity was determined. Results are depicted in FIG. 4.

Intestinal inflammatory status was determined with faecal MPO activity. FIG. 4 shows that additivated feed of the invention gave comparable results with the control diet including antibiotics.

Average daily weight gain was of 220 g/day in (C) group, 267 g/day in (AMA) group and 269 g/day in (T) group (an increase of 22% compared to (C) group). Average daily feed intake was 312 g/day in (C) group, 363 g/day in (AMA) group and 395 g/day in (T) group (an increase of 26% compared to (C) group and of 9% compared to (AMA) group).

These assays allow concluding that with the animal feed comprising HT, MA and OA at the indicated proportions, use of antibiotics can be reduced or even avoided without the loss of animals and maintaining or even improving performance of animals (note the daily gain in piglets of (T) group). Furthermore, the use of feed comprising HT, MA and OA clearly stimulates feed intake in animals even submitted to a severe challenge mimicking real infectious conditions common in animal production.

This assay also allowed concluding that the additive can be used in animals of low body weight at birth.

Example 6. Assay for Analysis of Reduction of the Dependency of Use of Medication in Piglet/Weaner Diets in Field Conditions A more exhaustive assay (n=250) was performed following a schedule similar to that of Examples 3 and 4 in order to see if medication could effectively be reduced with the animal feed additivated as proposed by the invention in commercial conditions.

At day 0 of life, lactating piglets were divided in two different groups: I) (C) piglets fed with control diets, from day 0 to day 63 of life and II) (T) piglets fed with control feed supplemented with formulation K (500 ppm) including HT/MA/OA. Formulation K consisted in a preparation containing 2.3% w/w of HT, 11.4% w/w of MA and 4.2% w/w of OA. Final ratios of detected amounts of MA and HT (MA/HT) and of amounts of MA and OA (MA/OA) were, respectively, 5.0 and 2.7. In this assay animals received a creep-feed from day 0 to day 21 (weaning), same creep-feed from day 22 to 28, a prestarter diet was followed from day 29 to day 41 and finally, a starter diet was offered at day 41 until the end of assay (day 63). Thus, animals faced three dietary changes after weaning Next Table 3 shows the additives used in each of the diets:

| Treatment | N | Creep-Feed | Prestarter | Starter |
|---|---|---|---|---|
| C | 250 | Amoxicilin (150 ppm) | Amoxicilin (400 ppm) | Amoxicilin (300 ppm) |
| | | Colistin (120 ppm) | Colistin (100 ppm) | ZnO (2500 ppm) |
| | | ZnO (2500 ppm) | ZnO (2500 ppm) | Apramicin (100 ppm) |
| | | Florphenicol (80 ppm) | Florphenicol (80 ppm) | |
| T | 250 | Amoxicilin (150 ppm) | Amoxicilin (400 ppm) | *HT/MA/OA |
| | | Colistin (120 ppm) | Colistin (100 ppm) | additive (500 ppm) |
| | | ZnO (2500 ppm) | ZnO (2500 ppm) | |
| | | Florphenicol (80 ppm) | Florphenicol (80 ppm) | |
| | | *HT/MA/OA | *HT/MA/OA | |
| | | additive (500 ppm) | additive (500 ppm) | |

*HT/MA/OA additive (500 ppm of a preparation containing 2.3% w/w of HT, 11.4% w/w of MA and 4.2% of OA). Ratio of detected amounts MA/HT and MA/OA was of 4.8 and 2.6, respectively. BW at different days and at the end of assay (final BW) are listed in Table 4.

TABLE 4

| Body weight (BW) at different dates. | | |
| --- | --- | --- |
| BWX at day (X) | Control | Treatment of invention |
| BW0 | 5.75 | 5.79 |
| BW6 | 6.03 | 6.09 |
| BW19 | 8.90 | 9.10 |
| BW42 | 18.19 | 19.02 |

Data allow concluding that there was an increase in final BW of 4% in piglets receiving feed with HT, MA and OA, confirming that proposed additive allows a reduction in feed medication maintaining or even improving piglets performance.

Example 7. Assay in Piglets/Weaners. Assay for Validation of Effects in Mortality Pre and Post-Weaning in Field Conditions In a similar assay, piglets were divided in two experimental group: I) (C, n=113) piglets fed with control diets (no medication added) and II) (T, n=113) piglets fed with control diet supplemented with H (2500 ppm) including HT/MA/OA (0.36% w/w of HT, 2.76% w/w of MA and 1.10% w/w of OA). Final ratios of detected amounts of MA and HT (MA/HT) and of amounts of MA and OA (MA/OA) were, respectively, 7.7 and 2.5. In this assay animals received a creep feed during lactation, after cross fostering practices (from day 3 to day 21 of life), then changed to a prestarter diet from day 22 to day 35 and finally a starter diet from day 36 to day 63 (end of the experiment).

Mortality reduction and average daily weight gain (ADG) was determined in (C) vs (T) groups:

Mortality reduction before weaning was of 9.72% vs 4.63%

Mortality reduction after weaning was of 4.91% vs 1.09%

ADG increase before weaning was of 0.176 vs 0.203 g/day

ADG increase after weaning 0.296 vs 0.325 g/day, days 0 to 42 post weaning.

Therefore, with the three ingredients HT, MA and OA used in combination, mortality of animals in sensitive stages of life was highly reduced and at the same time an increase in daily weight gain was observed.

Example 8. Assay in Poultry. Turkey Final BW 200 one-day-old turkeys were assigned to 2 experimental treatments from week 3 until week 14 of life (4 groups/treatment, with 25 birds/group): I) (C) animals fed with control diet; II) (T) animals fed control diet supplemented with formulation F (2500 ppm in feed). Formulation F consisted in a preparation containing HT/MA/OA (0.36% w/w of HT, 2.76% w/w of MA and 1.10% w/w of OA). Final ratios of detected amounts of MA and HT (MA/HT) and of amounts of MA and OA (MA/OA) were, respectively, 7.7 and 2.5.

The final BW of (C) group vs (T) group receiving feed with HT, MA and OA was of 9.24 Kg vs 9.50 Kg (increase of 2.8%).

From these results we can conclude that the use of HT/MA/OA in feed improves the performance of Turkeys as already shown for piglets in examples 4, 5 and 7.

Example 9. Assay in Poultry. Broilers Final BW. Dietary Challenge 490 one-day-old broiler chickens were assigned to 2 experimental treatments from day 0 until day 35 of age (7 groups/treatment, with 35 birds/group): I) (C) animals fed with a control+challenge diet (based on rye-wheat-barley and soybean meal without enzymes, only in the grower phase); II) (T) animals fed with the same control+challenge diet, both supplemented with formulation L (250 ppm in feed). Two different diets were offered to broilers: a started diet from day 0 to day 14, and a grower diet from day 15 to day 35. Formulation L consisted in a preparation containing HT/MA/OA (2.2% w/w of HT, 10.8% w/w of MA and 4.1% w/w of OA). Final ratios of detected amounts of MA and HT (MA/HT) and of amounts of MA and OA (MA/OA) were, respectively, 4.9 and 2.6.

The final BW of (C) group vs (T) group were of 2.39 Kg vs 2.42 Kg (increase of 1.4%).

Recorded results allow concluding that the use of HT/MA/OA in feed improves the performance of broilers, as already shown in example 8 for turkeys and in examples 4, 5 and 7 for piglets, even in conditions of dietary challenge.

Example 10. Assay in Broilers Challenged with *Eimeria* Spp 240 one-day-old broiler chickens were assigned to 3 experimental treatments from day 0 until day 28 of age (10 groups/treatment, with 8 birds/group): I) (C) animals fed with control diet; II) (T1) animals fed control diet supplemented with 500 ppm of formulation M comprising HT/MA/OA (1% w/w of HT, 5.8% w/w of MA and 2.7% w/w of OA) and III) (T2) animals fed control diet supplemented with 665 ppm of formulation N comprising MA/OA. (5.1% w/w of MA and 2.4% w/w of OA). Final ratios of detected amounts of MA and HT (MA/HT) and of amounts of MA and OA (MA/OA) were, respectively, 5.9 and 2.1 in diets for T1 and MA and OA (MA/OA) 2.1 in diets for T2 (HT was not present). Two different diets were offered to broilers: a started diet from day 0 to day 14, and a grower diet from day 15 to day 28.

At 0, 7 and 14 d post-hatch, birds were challenged with an oral gavage of a live *Eimeria* spp oocysts vaccine (Coccivac®-B52, Merck) at 1×, 4× and 16× of the manufacturer's recommendation dose, respectively.

Total feed intake was measured as grams of feed consumed during the total experimental period (28 days). Total feed intake in (C) group was 1779 g; in (T1) group was 1842 g and in (T2) group was 1767 g.

These results show an unexpected effect in the total feed intake due to the presence of HT. This increase in feed intake is of relevance in animals at very sensitive stages of life (transition to growers in piglets or before finishing diets in poultry) where any input (vaccination, infection challenge, social stress) may make them not to eat enough with the corresponding reduction in weight gain, or with the corresponding increase of susceptibility to diseases and illness (i.e., diarrhoea due to immature intestines).

Example 11. Assay with Broilers to Determine Mortality and Final Body Weight 660 one-day-old broiler chickens were assigned to 2 experimental treatments from day 0 until day 38 of age (2 groups/treatment, with 165 birds/group): I) (C) animals fed with control diet; II) (T) animals fed control diet supplemented with formulation F (1250 ppm in feed) containing 0.36% w/w of HT, 2.76% w/w of MA and 1.10% w/w of OA. Final ratios of detected amounts of MA and HT (MA/HT) and of amounts of MA and OA (MA/OA) were, respectively, 7.7 and 2.5. Four different diets were offered to broilers: a started diet from day 0 to day 11, a grower I diet from day 12 to day 21, a grower II diet from day 22 to day 32, and a finisher diet from day 33 to day 38.

Broilers in (T) group reached a final BW of 2.62 Kg in front of 2.59 Kg for (C) group.

The most surprising result was that the mortality reduction in broilers of (T) group (1.82% in front of 4.24% in (C) group).

Therefore, as previously demonstrated in piglets (Example 7), mortality was also considerably reduced in poultry while final BW were improved in these kind of animals (see Examples 8 and 9)

Example 12. Preparation of an Additive of the Invention and of Additivated Feedstuffs Including it In a ploughshare mixer, a liquid *Olea europaea* extract (90 kg) comprising HT from 1% to 20% w/w of HT was adsorbed onto silicic acid. A propionic acid-based preservative (0.5 kg) and a characteristic feed flavour (0.8 kg) of common use in domesticated animal feeding were also added at this point. Then a second *Olea europaea* solid extract (5 kg) comprising HT from 4.5% to 20% w/w of HT was also added to the previously adsorbed HT, to adjust the percentage by weight of HT in the final additive from 0.3% to 5.0%. A non-ethanolic solid extract of *Olea europaea* (105 kg) containing MA and OA was added to get in the final additive from 2.0% w/w to 20% w/w of MA and from 0.5% w/w to 15% w/w of OA. Other extracts of *Olea europaea* (i.e., ethanolic or with other extractant) to get in the final additive the indicated percentages of each of MA and OA can also be used. At the last step of the mixing process a palm-based oil binder comprising middle-chain fatty acid glycerides (2.5 kg) was added to the mixture of particles with MA, OA and HT. The mixture was finally sieved through a 2 mm sieve to adjust particle size according to the following distribution: a mean particle size higher than 500 μm, and where more than 70% of the particles have a particle diameter higher than 400 μm and less than 30% of the particles have a particle diameter lower than 250 μm. Relative humidity (measured by Karl Fisher titration method) was between 10-20%.

This additive had the adequate consistency to be processed in the production of common feedstuffs, since it could be mixed with the rest of the ingredients of the feedstuff without any dustiness problems.

These particulate additives of the invention, with the binders and specific particle size distribution, allow an economic and reliable way to add the three ingredients of interest (HT, MA and OA) in any feed for domesticated animals at very sensitive and vulnerable phases of their lives. This is finally translated to a reduction of the production loss of breeders, since animals are prepared to face many of the challenges during the growing-up phase and the finishing.

Example 13. Assay with Weaners and Different Amounts of Additive in Feedstuff 8 weaners in transition and up to 50 days of life were fed as follows:
Control diet (no additive) and control diet supplemented with one of 0.5 kg/T of feedstuff;
1.0 Kg/T of feedstuff and 2.0 Kg/T of feedstuff
The additive contained 2.6% w/w of HT, 9.9% w/w of MA and 2.3% w/w of OA. Doses were 500 ppm, 1000 ppm and 2000 ppm. Final ratios were the same in all formulations but amount of active compounds differed.

Specific amounts of each of the ingredients were:
500 ppm (13 ppm HT, 49.5 ppm MA, 11.5 OA ppm)
1000 ppm (26 ppm HT, 99 ppm MA, 23 ppm OA)
2000 ppm (52 ppm HT, 198 ppm MA, 46 ppm OA)
Final body weight and intake of food were recorded:
Final BW (Control=9.7 Kg, Dose 500 ppm=10.6 Kg, Dose 1000 ppm=10.0 Kg,
Dose 2000 ppm=10.1 kg) Intake (Control=367 g/d, Dose 500 ppm=425 g/d, Dose 1000 ppm=378 g/d, Dose 2000 ppm=374 g/d)

These results show that the adequate proportion of the additive in the feedstuff and of the ingredients is important, as well as a top up amount in particular of maslinic acid. High amounts of additive and of maslinic acid made the weaners did not eat as in a dose of 500 ppm with MA under 75 ppms (i.e., 49.5 ppm). Intake at these early ages is critical and a low intake is finally translated to a lower protection degree.

Example 14. Assay in Weaners with an Additive Free of Hydroxytyrosol (HT)

An experimental assay was performed with weaners at transition and up to 63 days of life. One group (n=16) received a feedstuff supplemented with H (2500 ppm) including HT/MA/OA (0.36% w/w of HT, 2.76% w/w of MA and 1.10% w/w of OA). Final ratios of detected amounts of MA and HT (MA/HT) and of amounts of MA and OA (MA/OA) were, respectively, 7.7 and 2.5. In this assay animals received a creep feed from day 21 to day 31 of life, then changed to a prestarter diet from day 31 to day 42 and finally a starter diet from day 42 to day 63 (end of the experiment) and another group (n=16) received the same feedstuff with an additive without HT.

Intake and final body weight were recorded:
Intake of group with complete additive: 535 g/day
Body weight (day 42) of group with complete additive: 19.9 Kg
Intake of group with complete additive: 473 g/day
Body weight (day 42) of group with complete additive: 18.7 Kg These results show that the presence of the three ingredients is important for the correct performance of the growing up of the animals.

CITATION LIST

Patent Literature

CN102578387
WO2007/096446
US2010/0116312

Non Patent Literature

Pohl et al. (2017). Early weaning stress induces chronic functional diarrhea, intestinal barrier defects, and increased mast cell activity in a porcine model of early life adversity. *Neurogastroenterology% Motility*. E13118. DOI. 10.1111/nmo.13118.
Rufino-Palomares, E. E. et al. Maslinic acid, a natural triterpene, and ration size increased growth and protein turnover of white muscle in gilthead sea bream (*Sparus aurata*). Aquac. Nutr. 18, 568-580 (2012)

EFSA Journal 2014; 12(5):3702 and/or http://www.welfare-
    qualitynetwork.net/en-us/reports/assessment-protocols/

What is claimed is:

1. A feedstuff comprising an additive for a domesticated
animal at a non-reproductive age, the additive comprising
hydroxytyrosol, maslinic acid and oleanolic acid, wherein
hydroxytyrosol is in a percentage by weight from 0.3% to
5.0% w/w, maslinic acid is in a percentage by weight from
2.0% to 20% w/w, and oleanolic acid is in a percentage by
weight from 0.5% to 15% w/w to obtain a final feedstuff, all
percentages in relation to the total weight of the additive;
    wherein maslinic acid and hydroxytyrosol are in a weight
        ratio (MA/HT) in the final feedstuff from 2:1 to 20:1
        and maslinic acid and oleanolic acid are in a weight
        ratio (MA/OA) in the final feedstuff from 1:1 to 10:1,
        and wherein the feedstuff comprises an amount of
        additive giving hydroxytyrosol at a concentration from
        2.5 ppm to 20 ppm, maslinic acid at a concentration of
        at least 10 ppm and up to 75 ppm, and a concentration
        of oleanolic acid of at least 5 ppm and up to 35 ppm,
        all concentrations in relation to the total weight of the
        feedstuff.

2. The feedstuff according to claim 1, wherein maslinic
acid and hydroxytyrosol are in a weight ratio (MA/HT) in
the final feedstuff from 2.0:1 to 4.0:1, and the ratio of
maslinic acid and oleanolic acid (MA/OA) in the final
feedstuff is from 1.0:1 to 2.0:1.

3. The feedstuff according to claim 1, wherein the weight
ratio of maslinic acid and hydroxytyrosol (MA/HT) in the
final feedstuff is from 6.0:1 to 20.0:1, and the weight ratio
of maslinic acid and of oleanolic acid (MA/OA) in the final
feedstuff is from 1.0:1 to 2.0:1.

4. A method for preparing a feed for a domestical animal,
the method comprising adding to a first feed for a domesticated animal an additive comprising hydroxytyrosol,
maslinic acid and oleanolic acid, in which hydroxytyrosol is
in a percentage by weight from 0.3% to 5.0% w/w, maslinic
acid is in a percentage by weight from 2.0% to 20% w/w, and
oleanolic acid is in a percentage by weight from 0.5% to
15% w/w to obtain a final feed, all percentages in relation to
the total weight of the additive;
    wherein maslinic acid and hydroxytyrosol are in a weight
        ratio (MA/HT) from 2:1 to 20:1 in the final feed and
        maslinic acid and oleanolic acid are in a weight ratio
        (MA/OA) in the final feed from 1:1 to 10:1, and
    wherein the final feed comprises an amount of additive
        giving hydroxytyrosol at a concentration from 2.5 ppm
        to 20 ppm, maslinic acid at a concentration of at least
        10 ppm and up to 75 ppm, and a concentration of
        oleanolic acid of at least 5 ppm and up to 35 ppm, all
        concentrations in relation to the total weight of the final
        feed.

5. The method according to claim 4, wherein the feed is
for a piglet and/or a weaner.

6. The method according to claim 4, wherein the feed is
for a broiler from hatch to 35 days post-hatch.

7. The method according to claim 4, wherein the feed is
for a turkey from hatch to 84 days post-hatch.

8. The feedstuff according to claim 1, wherein the additive
comprises a binder and wherein the additive is in particulate
form with a mean particle size higher than 500 μm, and
where more than 70% of the particles have a particle
diameter higher than 400 μm and less than 30% of the
particles have a particle diameter lower than 250 μm.

9. The feedstuff according to claim 8, wherein the binder
is selected from the group consisting of a mineral oil,
petrolatum, vegetal origin oil and mixtures thereof.

*    *    *    *    *